US006555328B1

(12) United States Patent  
Keesler et al.

(10) Patent No.: US 6,555,328 B1
(45) Date of Patent: Apr. 29, 2003

(54) SCREENING METHODS FOR ALTERING CIRCADIAN RHYTHMS AND FOR HUMAN CASEIN KINASE I δ AND/OR ε PHOSPHORYLATION OF HUMAN CLOCK PROTEINS, PERIOD 1, -2 AND -3

(75) Inventors: George A. Keesler, Sommerville, NJ (US); Cesare Mondadori, Basking Ridge, NJ (US); Zhengbin Yao, Whitehouse Station, NJ (US); Fernando Camacho, Union, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 189 days.

(21) Appl. No.: 09/589,462

(22) Filed: Jun. 7, 2000

Related U.S. Application Data

(63) Continuation-in-part of application No. 09/327,745, filed on Jun. 8, 1999, now abandoned.

(51) Int. Cl.[7] .............................. C12Q 1/48; C12Q 1/42; C12Q 1/37
(52) U.S. Cl. .............................. 435/15; 435/21; 435/23; 435/24; 435/4; 435/255.1
(58) Field of Search .............................. 435/15, 21, 23, 435/24, 4, 255.1

(56) References Cited

FOREIGN PATENT DOCUMENTS

| WO | WO 99/57137 | * | 11/1999 |
| WO | 200075669 A1 | * | 6/2000 |

OTHER PUBLICATIONS

Cegielska Aleksandra et al., Autoinhibition of Casein Kinase I E (CKIE) is Relieved by Protein Phosphatases and Limited Proteolysis, The Journal of Biological Chemistry, vol. 273, No. 3, 1998; pp. 1357–1364.
Edery Isaac et al., Temporal Phosphorylation of the Drosophila Period Protein, Proc. Natl. Acad. Sci. USA, vol. 91, pp. 2260–2264, Mar. 1994.
Fish Kimberly J et al., Isolation and Charaterization of Human Casein Kinase IE (CKI), a Novel Member of the CKI Gene Family, The Journal of Biological Chemistry, vol. 270, No. 25, 1995; pp. 14875–14883.
Keesler George A, Nueroreport 11(5):951–955, Apr. 7, 2000 Phosphorylation and destabilization of Human Period I Clock Protein by Human Casein Kinase Ie.
Kloss Brian et al., The Drosophila Clock Gene Double–time Encodes a Protein Closely Related to Human Casein Kinase IE, Cell, vol. 94, Jul. 10, 1998, pp. 97–107.
Price Jeffrey L et al., Double–time Is a Novel Drosophila Clock Gene that Regulates Period Protein Accumulation, Cell, vol. 94, Jul. 10, 1998, pp. 97–107.
Reppert Steven M, Minireview A Clockwork Explosion!, Neuron, vol. 21, 1998, pp. 1–4.
Rivers Ann et al., Regulation of Casein Kinase I E and Casein Kinase I Delta by an In Vivo Futile Phosphorylation Cycle, J Biol Chem, vol. 273, Issue 26, Jun. 26, 1998, pp. 15980–15984.
Shearman Lauren P et al., Two period Homologs: Circadian Expression and Photic Regulation the Suprachiasmatic Nuclei, Neuron, vol. 19, Dec. 1997, pp. 1261–69.
Sugano Shoji et al., Protein Kinase CK2 Interacts with and Phosphorylates the Arabidopsis Circadian Clock–associated 1 Protein, Proc. Natl. Acad. Sci. USA, vol. 95, pp. 11020–11025, Sep. 1998.

* cited by examiner

Primary Examiner—Louise N. Leary
(74) Attorney, Agent, or Firm—Michael J. Schmelzer

(57) ABSTRACT

The present invention is directed to methods to identify test compounds that alter circadian rhythms of mammals, and more specifically, directed to methods for determining the ability of a test compound to alter hCKI δ and ε phosphorylation of a human Period protein. The present invention is also directed to a method for determining the ability of a test compound to selectively alter phosphorylation, interaction with, or alternatively degradation, of one or more human Period proteins relative to its ability to alter phosphorylation, interaction with, or alternatively degradation, of a different human Period protein.

57 Claims, 11 Drawing Sheets

FIG. 4A

M2 IP
HA Western

Flag-hPER1: −, +, +, Lysate
HA-hCKIε: +, −, +

◀ hCKIε

HA IP
M2 Western

Flag-hPER1: −, +, +, Lysate
HA-hCKIε: +, −, +

◀ hPER1

M2 IP
hCKIε Western

Flag-hPER1: −, +, +, Lysate
HA-hCKIε: +, −, +

◀ hCKIε

1 2 3 4

FIG. 4D hCKIε IP
M2 Western

Flag-hPER1: −, +, +, Lysate
HA-hCKIε: +, −, +

◀ hPER1

1 2 3 4

Period (Per)

- Critical component of Circadian clock.
- Point mutations in Period cause altered circadian rhythm.
- Per mRNA concentration is inversely correlated with period length in Drosophila.
- Per knockout mice have altered rhythm

CKIe/Period co-transfection secondary assay

Inhibition of Per Phosphorylation results in increased protein stability and levels.

SEQUENCE LISTING

<160> NUMBER OF SEQ ID NOS: 9

<210> SEQ ID NO 1
<211> LENGTH: 17
<212> TYPE: PRT
<213> ORGANISM: Homo sapiens

<400> SEQUENCE: 1

Ile Gln Glu Leu Ser Glu Gln Ile His Arg Leu Leu Leu Gln Pro Val
1               5                   10                  15

His

<210> SEQ ID NO 2
<211> LENGTH: 17
<212> TYPE: PRT
<213> ORGANISM: Homo sapiens

<400> SEQUENCE: 2

Ile Gln Glu Leu Thr Glu Gln Ile His Arg Leu Leu Leu Gln Pro Val
1               5                   10                  15

His

<210> SEQ ID NO 3
<211> LENGTH: 17
<212> TYPE: PRT
<213> ORGANISM: Homo sapiens

<400> SEQUENCE: 3

Ile Thr Glu Leu Gln Glu Gln Ile Tyr Lys Leu Leu Leu Gln Pro Val
1               5                   10                  15

His

<210> SEQ ID NO 4
<211> LENGTH: 10
<212> TYPE: PRT
<213> ORGANISM: Influenza virus

<400> SEQUENCE: 4

Tyr Pro Asp Tyr Asp Val Pro Asp Tyr Ala
1               5                   10

<210> SEQ ID NO 5
<211> LENGTH: 37
<212> TYPE: DNA
<213> ORGANISM: Homo sapiens

<400> SEQUENCE: 5
atctagatct agaatgaatg gatacgcgga atttccg                              37

<210> SEQ ID NO 6
<211> LENGTH: 34
<212> TYPE: DNA
<213> ORGANISM: Homo sapiens

<400> SEQUENCE: 6
tctgctcgag tcaaggggga tccattttcg tctt                                 34

<210> SEQ ID NO 7
<211> LENGTH: 22
<212> TYPE: DNA
<213> ORGANISM: Rattus rattus

```
<400> SEQUENCE: 7
tctggttaag gctgctgaca ag                                          22

<210> SEQ ID NO 8
<211> LENGTH: 20
<212> TYPE: DNA
<213> ORGANISM: Rattus rattus

<400> SEQUENCE: 8
gtgtagcccc aaccctgtga                                             20

<210> SEQ ID NO 9
<211> LENGTH: 22
<212> TYPE: DNA
<213> ORGANISM: Rattus rattus

<400> SEQUENCE: 9
tccaaatccc agctgagccc ga                                          22
```

SCREENING METHODS FOR ALTERING CIRCADIAN RHYTHMS AND FOR HUMAN CASEIN KINASE I δ AND/OR ε PHOSPHORYLATION OF HUMAN CLOCK PROTEINS, PERIOD 1, -2 AND -3

This application is a continuation-in-part of patent application Ser. No. 09/327,745 filed Jun. 8, 1999 now abandoned.

FIELD OF THE INVENTION

This invention relates to methods to identify test compounds that alter circadian rhythms of mammals, and more specifically that alter the ability of human casein kinase I δ and/or ε to phosphorylate the Human Clock proteins, human Period 1, human Period 2 and human Period 3.

BACKGROUND OF THE INVENTION

Circadian rhythms generated by endogenous biological pacemakers are present in a number of diverse organisms including humans, fungi, insects and bacteria (Dunlap, J. C. (1999) Cell, 96, 271–290; Hastings, J. W., et al., (1991) in Neural and Integrative Animal Physiology, ed. Prosser, C. L. (New York: Wiley-Liss), pp.435–546; Allada, R., et al., (1998) Cell, 93, 791–804; Kondo, T., et al., (1994) Science, 266, 1233–1236; Crosthwaite, S. K., et al., (1997) Science, 276, 763–769). Circadian clocks are essential in maintaining biological rhythms. They are self-sustaining and constant even under conditions of total darkness but can be entrained by environmental signals such as light and temperature changes. Endogenous clocks control patterns of activity including daily fluctuations in behavior, food intake and sleep/wake cycle as well as physiological changes such as hormone secretion, and fluctuations in body temperature (Hastings, M., (1997) Trends Neurosci. 20, 459–464; Kondo, T., et al., (1993) Proc. Natl. Acad. Sci. USA, 90, 5672–5676.; Reppert, S. M., & Weaver, D. R. (1997) Cell, 89, 487–490).

Genetic and molecular studies in Drosophila have allowed for the elucidation of some of the genes involved in circadian rhythmicity. What has emerged from these studies is a pathway closely auto-regulated and comprised of a transcription/translation-based negative feed back loop (Dunlap, J. C. (1999) Cell, 96, 271–290; Dunlap, J. C. (1996) Annu. Rev. Genet. 30, 579–601; Hall, J. C. (1996) Neuron, 17, 799–802). Two critical components of the central clock are molecules termed Period or PER and Timeless or TIM.

The per locus, first discovered in Drosophila, is a necessary element in controlling circadian rhythms in adult eclosion behavior and locomotor activity (Konopka, R. J., & Benzer, S. (1971) Proc. Natl. Acad. Sci. USA 68, 2112–2116). Missense mutations of PER can either shorten (per$^S$) or lengthen (per$^L$) the period of circadian rhythms, while nonsense mutations (per$^o$) cause arrhythmicity in their behaviors (Hall, J. C. (1995) Trends Neurosci. 18, 230–240). In the suprachiasmatic nuclei (SCN) of mammals, three PER homologues, per1, per2, and per3 have been identified. The protein products of these mammalian genes share several regions of homology to each other (Zylka, M. J., et al., (1998) Neuron 20, 1103–1110; Albrecht, U., et al., (1997) Cell 91, 1055–1064.). Per mRNA and protein levels oscillate during the daily cycle, but only PER1 and PER2 oscillate in response to light (Zylka, M. J., et al., (1998) Neuron 20, 1103–1110., Shearman, L. P., et al., (1997) Neuron 19, 1261–1269).

All PER proteins contain a protein/protein interacting region called the PAS domain that is necessary for dimer formation (Zylka, M. J., et al., (1998) Neuron 20, 1103–1110.). Another PAS containing protein, TIM was isolated by a yeast two-hybrid genetic screen using PER as a bait (Gekakis, N., et al., (1995) Science 270, 811–815). As PER protein levels increase, PER forms heterodimers with TIM. TIM/PER heterodimer formation is required for PER regulation because mutations in tim, cause a loss in circadian rhythm which is accompanied by a loss of per mRNA oscillation and the inability of PER to undergo nuclear translocation (Sangoram, A. M., et al., (1998) Neuron 21, 1101–1113; Zylka, M. J., et al., (1998) Neuron 21, 1115–1122).

Recently, several additional molecular components of circadian rhythmicity including CLOCK and BMAL/MOP3 have been discovered using genetic screening and biochemical characterization (Gekakis, N., et al., (1998) Science 280, 1564–1569; King, D. P., et al., (1997) Cell 89, 641–653; Allada, R., et al., (1998) Cell 93, 791–804).

Subsequent studies shed light on how PER is regulated at transcriptional levels. CLOCK and BMAL/MOP3, both contain basic-helix-loop-helix domain, a PAS domain, and form heterodimers to each other. Once PER is transcribed, translated and accumulated, PER translocates to the nucleus and binds to CLOCK through their common PAS domains and down regulates its own transcription, forming a negative feedback loop (Allada, R., et al., (1998) Cell 93, 791–804; Darlington, T. K., et al., (1998) Science 280, 1599–1603; Hao, H., et al., (1997) Mol. Cell. Biol. 17, 3687–3693; Jin, X., et al., (1999) Cell 96, 57–68.).

In addition, PER is modified and regulated at post-translational levels. Both PER and TIM appear to undergo phosphorylation which is effected by circadian oscillation (Edery, I., et al., (1994) Proc. Natl. Acad. Sci. USA 91, 2260–2264; Lee, C., et al., (1998) Neuron 21, 857–867). A Drosophila kinase termed double time (DBT) was recently cloned (Price, J. L., et al., (1998) Cell 94, 83–95, Kloss, B., et al., (1998) Cell 94, 97–107). Mutations in DBT cause either shortened or lengthened period of the behavioral rhythm. A P-element insertion mutation in DBT abolishes the circadian oscillations of PER in larval brain, indicating that DBT is an essential component of the Drosophila clock. PER accumulates in these mutants to high levels and is hypophosphorylated. DBT has not been shown to directly phosphorylate PER. CKIε is a closely related homologue of DBT in mammals (Kloss, B., et al., (1998) Cell 94, 97–107). CKIε and DBT are 86% homologus at the amino acid level in the kinase domain. hCKIε, first identified by Fish et al, is one of several CKI isoforms (α, β, γ, δ) which has serine/threonine protein kinase activity (Fish, K. J., et al., (1995) J. Biol. Chem. 270, 14875–14883; Rowles, J., et al., (1991) Proc. Natl. Acad. Sci. USA 88, 9548–9552). CKIs are involved in regulation of cellular DNA metabolism. Saccharomyces mutants with defective a HRR25 gene, a homologue to mammalian CKI, show sensitivity to double-stranded DNA breaks (Hoekstra, M. F., et al., (1991) Science 253, 1031–1034). Several in vitro substrates for hCKI have been identified which include RNA polymerases I and II, p53, IkBα, and simian virus 40 large T antigen. However, very little evidence exist which correlates hCKI phosphorylation to changes in substrate function, and to date, no clock genes have been shown to be hCKI δ and ε substrates.

Circadian rhythms are controlled by sequential phosphorylation of, and alterations of protein levels of, certain key proteins in the circadian pathway. Period (PER), a central component of the circadian clock pathway, undergoes daily oscillation in abundance and phosphorylation state. PER genes have been identified in Drosophila PER, designated dPER, mouse PER, designated mPER, and human PER, designated hPER. In Drosophila there is only one PER, which has most homology to the PER1 proteins. Both humans and mice have three PERs, designated PER 1, 2 and 3.

BRIEF SUMMARY OF THE INVENTION

The present invention is directed to discovery that hCKI δ and ε phosphorylate human Period proteins and that phosphorylated human Period proteins are degraded. As a result, the present invention is directed to methods to identify test compounds that alter circadian rhythms of mammals, and more specifically, directed to methods for determining the ability of a test compound to alter hCKI δ and ε phosphorylation of a human Period protein. The present invention is also directed to a method for determining the ability of a test compound to alter degradation of a phosphorylated human Period protein. The present invention is also directed to a method for determing the ability of a test compound to selectively alter phosphorylation, or alternatively degradation, of one or more human Period proteins relative to its ability to alter phosphorylation, or alternatively degradation, of a different human Period protein and subsequently alter the circadian rhythm of a mnammal.

Figure 1A:
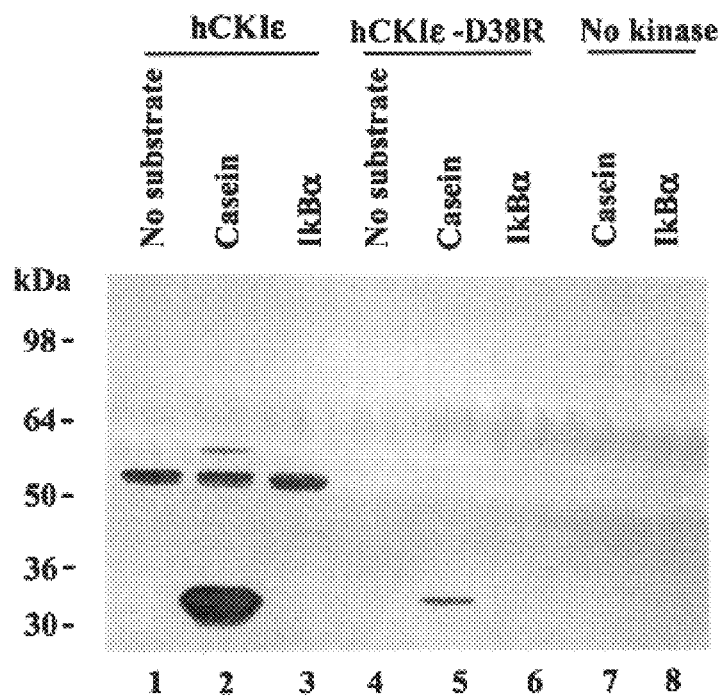
FIG. 1. In Vitro Phosphorylation of Casein, IkBα, and hPER1 by Recombinant hCMIε

Purification of recombinant casein kinase(s) and kinase assays conditions are described in the Materials and Methods, below. (A) hCKIε (lanes 1 to 3), hCKIε-K38Rε (lanes 4–6), or buffer control (lanes 7 and 8) is incubated either alone (lanes 1 and 4), with casein (lanes 2 and 5), or with IkBα (lanes 3 and 6), and kinase assays are performed as described in Material and Methods. Molecular weight markers are indicated to the left. (B) Lysates from 293T cells transfected with vector (lanes 1, 4 and 8), luciferase (lanes 2, 5 and 9) or hPER1 (lanes 3, 6, and 10) are prepared and immunoprecipitated using the M2 anti-Flag mAb and kinase assays are performed with hCKIε (lanes 1 to 6), hCKIε-K38Rε (lane 7) or buffer control (lanes 8–10). Immunoprecipitates are heat-inactivated at 65° C. for 30 min prior to the kinase assay (lanes 4–6). Samples are resolved by 12% SDS-PAGE. The gel is stained by Coomassie R-250, dried and autoradiographed.

FIG. 2. (A and B) Western Blot Analysis of hPER1 and hCKIε

293T cells are transfected with hPER1 and vector (lane 1), hPER1 and hCKIε (lane 2), hPER1 and hCKIε-K38R (lane 3), vector and hCKIε (lane 4), or vector and hCKIε-K38R (lane 5). At 24 hr post-transfection, cells are harvested and lysates are prepared as described in the Materials and Methods. 40 μg of total 293T lysate are loaded onto a 3–8% gradient NU-PAGE. Proteins are transferred to PVDF membranes and Western blotted using the M2 anti-Flag mAb (1:1000) or anti-hCKIε mAb (1:750). (C) Lambda phosphatase treatment of hPER1. 293T cells are transfected with hPER1 and vector (lanes 1 and 4), hPER1 and hCKIε (lanes 2 and 5), or hPER1 and hCKIε-K38R (lanes 3 and 6) and labeled with [$^{35}$S]methionine (250 μCi/ml). Lysate is immunoprecipitated using the M2 anti-Flag mAb and then either treated with recombinant lambda phosphatase (lanes 4, 5 and 6) or mock treated (lanes 1, 2 and 3).

FIG. 3. Pulse-chase Labeling of hPER1 Cotransfected with hCKIε

293T cells are co-transfected with either hPER1 and vector (panel A) or hPER1 and hCKIε (panel B). Three hours post transfection, 293T cells are pulse labeled with [$^{35}$S]methionine and cysteine (1000 μCi/ml) for 30 min and then chased for the times indicated at the top of each gel. Cells are lysed and immunoprecipitated with M2 anti-Flag mAb and hPER1 is resolved on 8% SDS-PAGE. Molecular weight markers are indicated to the left. (C) Bar graph representing a phosphoimaging scan of the area surrounding and including the hPER1 band from each lane. Bars (2–30 hr) are based on the percentage of total counts per minute (cpm) as compared to counts of the zero time point. Solid bars indicate hPER1 co-transfected with vector. Cross-hatched bars indicate hPER1 co-transfected with hCKIε.

FIG. 4. Protein Interaction between hPER1 and hCKIε (A, B, C and D)

293T cells are transfected with vector and hCKIε (lane 1), vector and hPER1 (lane 2), and hCKIε and hPER1 (lane 3). 24 hr post-transfection, cells are harvested and lysates are prepared. Lysates are immunoprecipitated with M2 anti-Flag mAb (panels A and C), HA mAb (panel B), or with anti-hCKIε mAb (panel D) and Western blotted with anti-HA mAb (panel A), M2 anti-Flag mAb (panel B and D), or anti-hCKIε mAb (panel C). In lane 4, Western blot analysis is performed on crude lysates before immunoprecipitation with the mAb indicated. All proteins are resolved on a 10% SDS-PAGE.

Figure 5A:
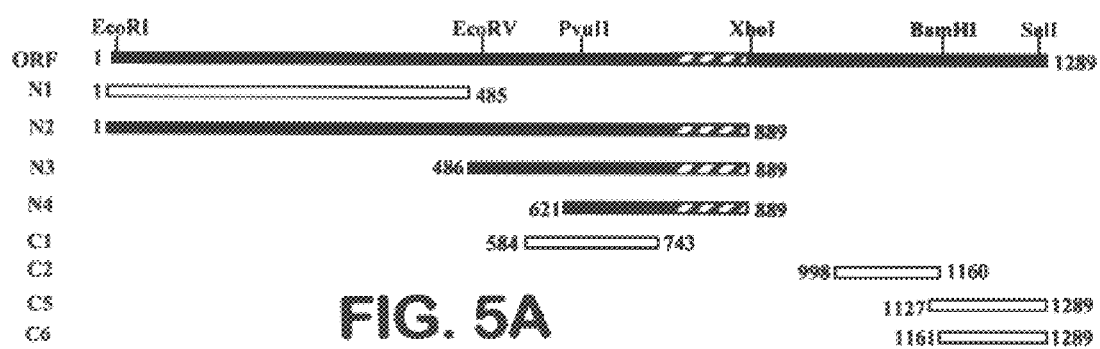
Figure 5B:
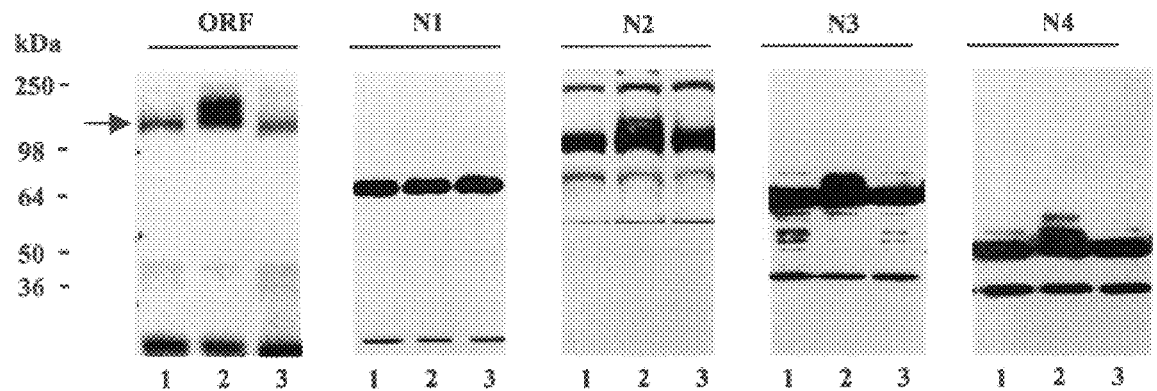
Figure 5C:
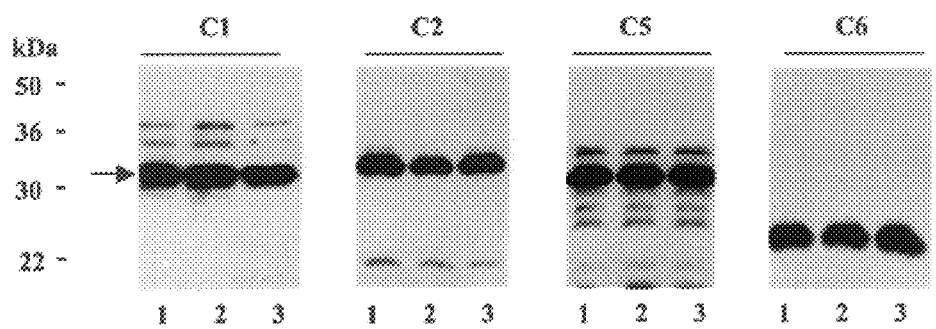

FIG. 5. Mapping of the hCKIε Phosphorylation Sites (A) Schematic representation of the recombinant truncated hPER1 mutants. Truncation mutants are constructed as described in the Materials and Methods, below. ORF indicates the complete open reading frame of hPER1, amino acid residues 1 to 1289. Restriction sites used for the generation of N1, N2, N3, N4, and C5 are indicated in Table 1. Open bars represent mutants that did not show molecular mass shifts. Solid bars represent mutants that did show molecular mass shifts. Crossed-hatched area of ORF, N2, N3, and N4 represent the region of putative phosphorylation of hPER1 by hCKε. (B) AND (C) Western blot analysis of co-transfected hPER1 truncation mutants from 293T lysates. 293T cells are co-transfected with hPER1 and vector (lane 1), hPER1 and hCKIε (lane 2), or hPER1 and hCKIε-K38R (lane 3) and are analyzed by Western blot analysis using M2 anti-Flag mAb. Molecular weight markers are indicated on the left. Arrows indicate the position of migration of each truncated mutant protein. FIG. 5B depicts hPER1 ORF and mutants N1, N2, N3, and N4. FIG. 5C depicts mutants C1, C2, C5, and C6. hPER1 ORF and mutants N1, and N2 are routinely resolved on a 10% SDS-PAGE, while hPER1 mutants N3, N4, C1, C2, C5, and C6 are routinely resolved on a 12% SDS-PAGE.

Figure 6:
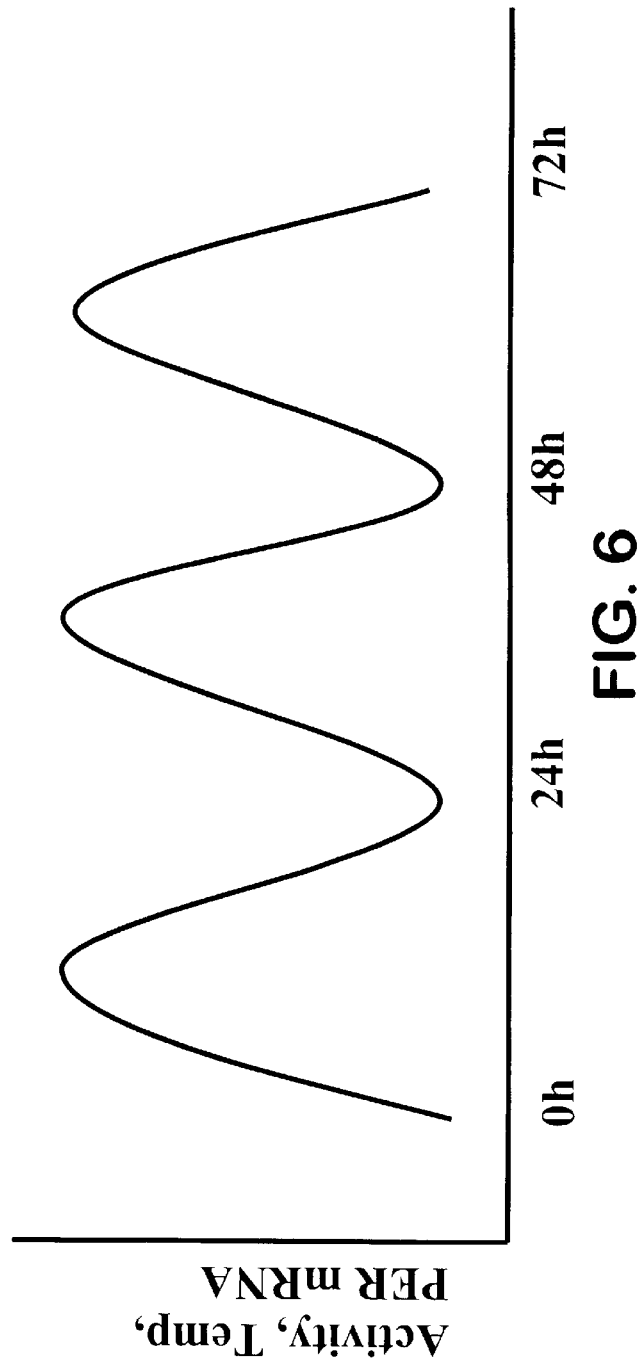

FIG. 6 Period mRNA Concentration

Time is given in hours on the bottom axis; the other axis is the activity, body temperature and Per mRNA levels over time. Per mRNA levels oscillate over a twenty-four hour period, and are inversely correlated with period length in Drosophila. Similar oscillations are observed in normal Per mice; however, Per knockout mice have an altered circadian rhythm.

Figure 7:
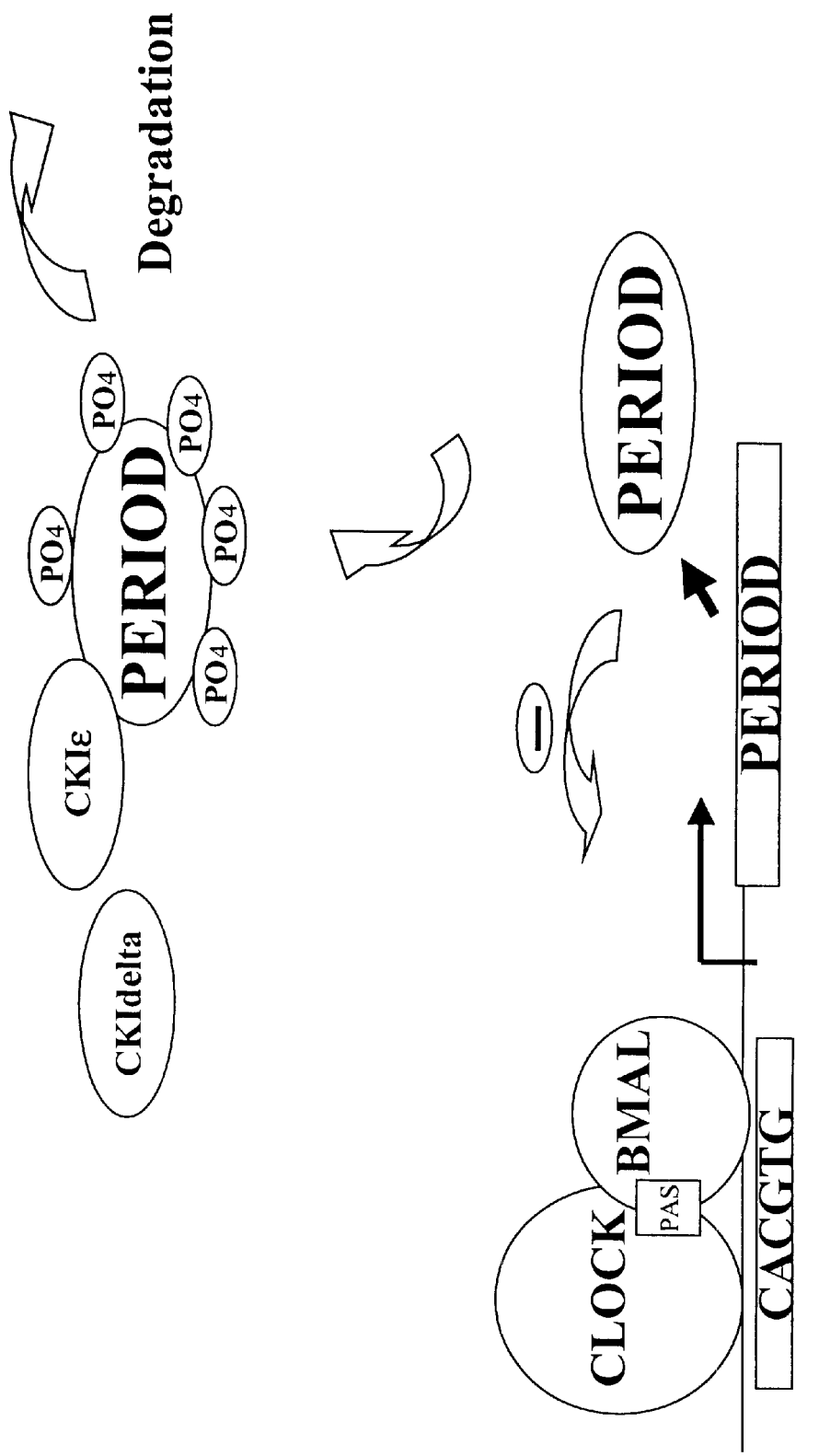

FIG. 7 Clock Protein Pathway

This is a schematic representation of the Clock protein pathway. hCKI δ and/or ε phosphorylate Period, as represented by PO$_4$, resulting in its degradation. Clock and BMal interract in the PAS domain, and initiate transcription of Period mRNA, resulting in increased levels of Period protein.

Figure 8:
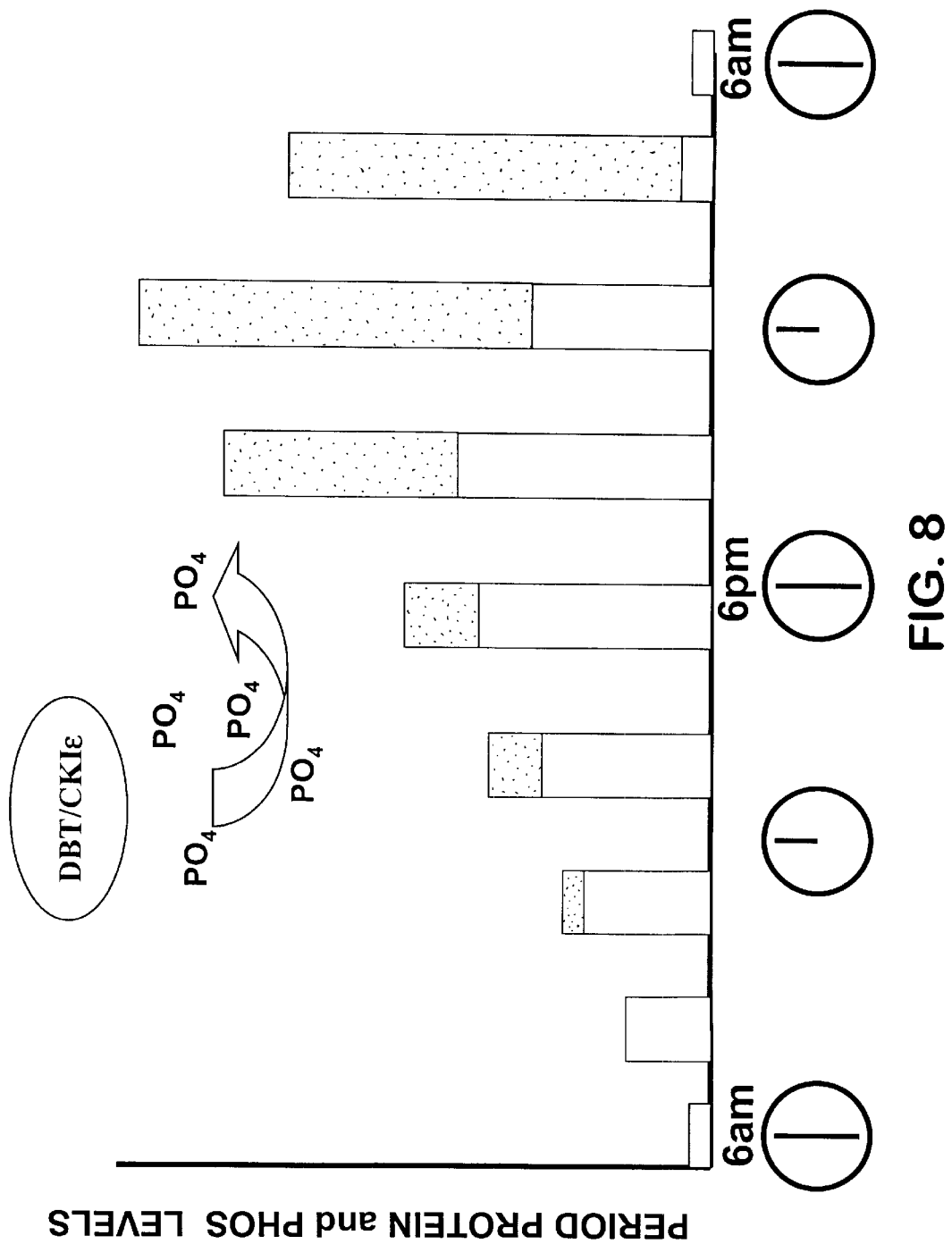

FIG. 8 Period Protein and Phosphate Levels Over Time

The bottom axis is time in hours over a twenty-four hour period; the other axis is Period protein (indicated in white) and phosphorylation levels (indicated in color). At the beginning of the circadian cycle, Period protein level is low, and relatively unphosphorylated. As Period protein levels increase to peak around 8 pm, relative phosphorylation of the Period protein also increases, and continues as Period protein levels decrease.

Figure 9:
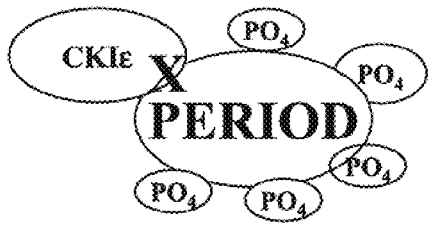
Figure 9:
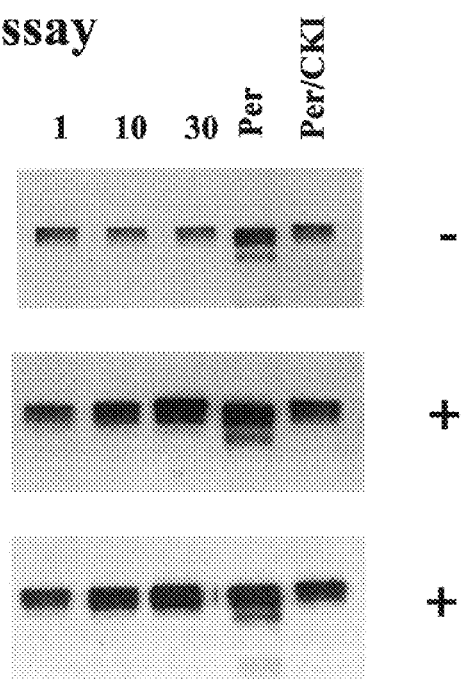

FIG. 9 CKIε/Human Period 1 Co-transfection

The top right panel shows hPer1 phosphorylation. The first column shows 1 uM of test compound; the second column shows 10 uM of test compound; the third column shows 30 uM of test compound; the fourth column shows Per alone; the fifth and last column shows Per and hCKIε. The top right panel shows a control test compound. The middle panel shows CKI ε inhibitor test compound S943166 and the bottom right panel shows CKI ε inhibitor test compound W0236. These results demonstate that inhibition of Per phosphorylation results in increased protein stability and levels.

Figure 10:
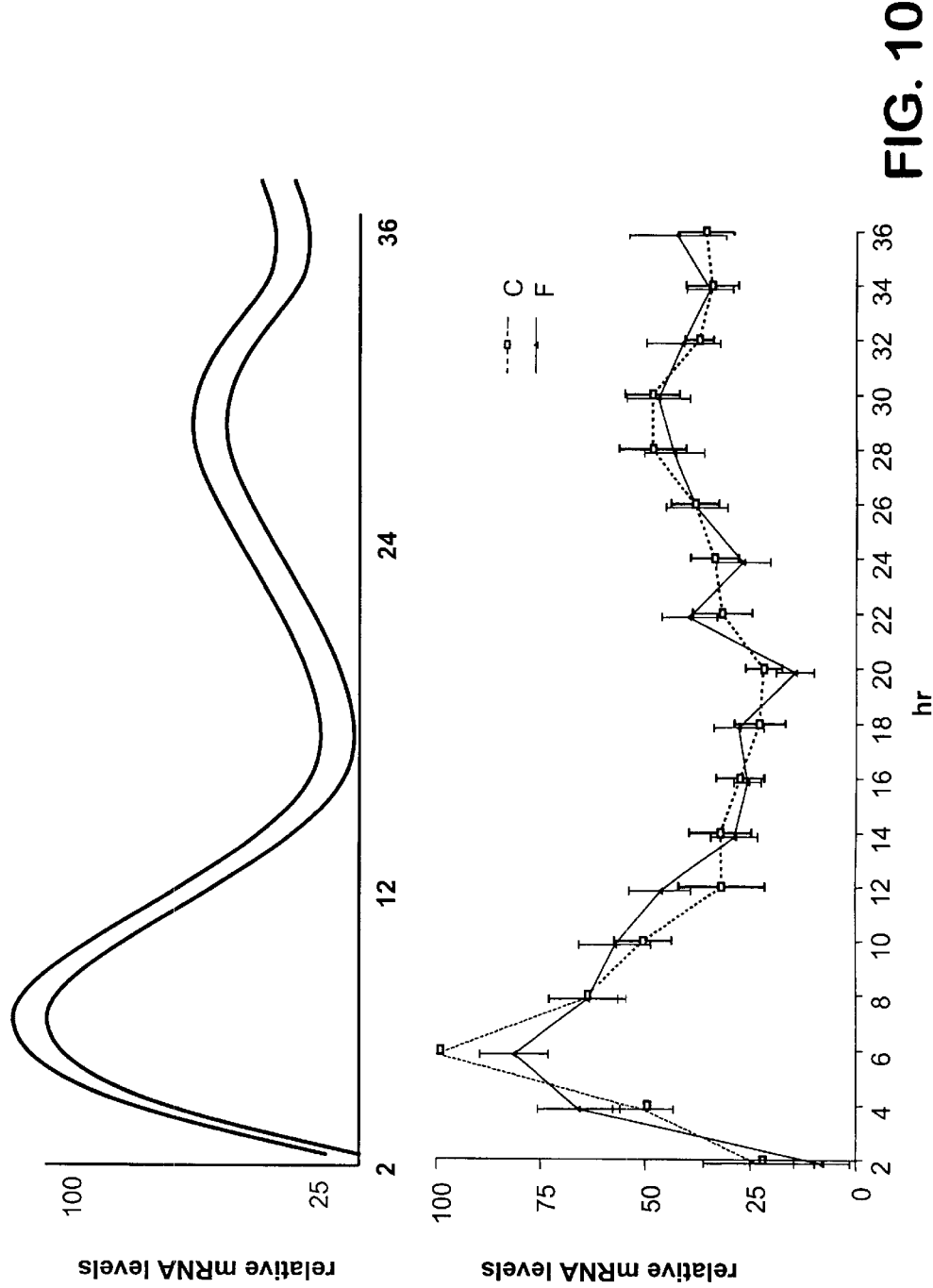

FIG. 10 Human Period mRNA Levels

The top graph provides a pictorial representation of the data presented in the bottom graph. The bottom axis is time in hours; the other axis is the relative real-time endogenous mRNA levels of hPER1 either Rat1 fibroblast or Rat SCN (suprachiasmatic nucleus) as determined by RT-PCR. Two test compounds are represented; the test compound represented by boxes is "C" which is added to the cells at 10 uM, the second test compound is represented by triangles is "F" (Fluoxitin) which is added to the cells at 10 uM. The circadian rhythm of cultured cells decreases over time, hence the amplitude of the response decreases over time. These results show that the control compound do not alter CKI activity also do not alter the circadian rhythm of cells.

Figure 11:
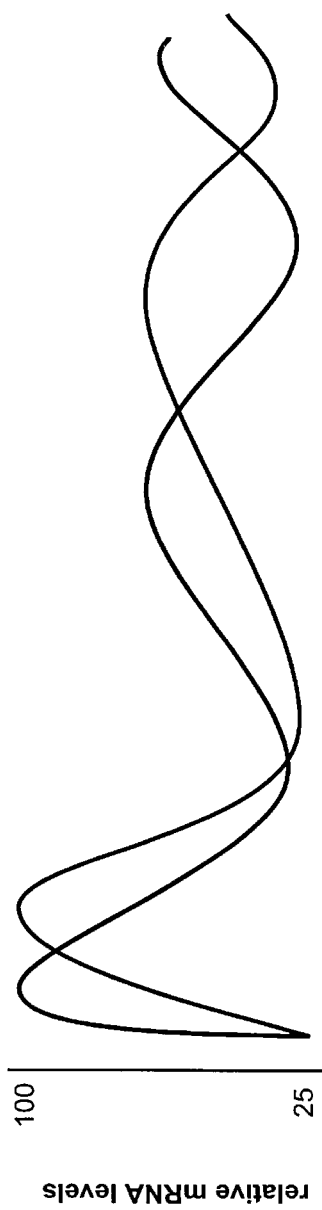
Figure 11:
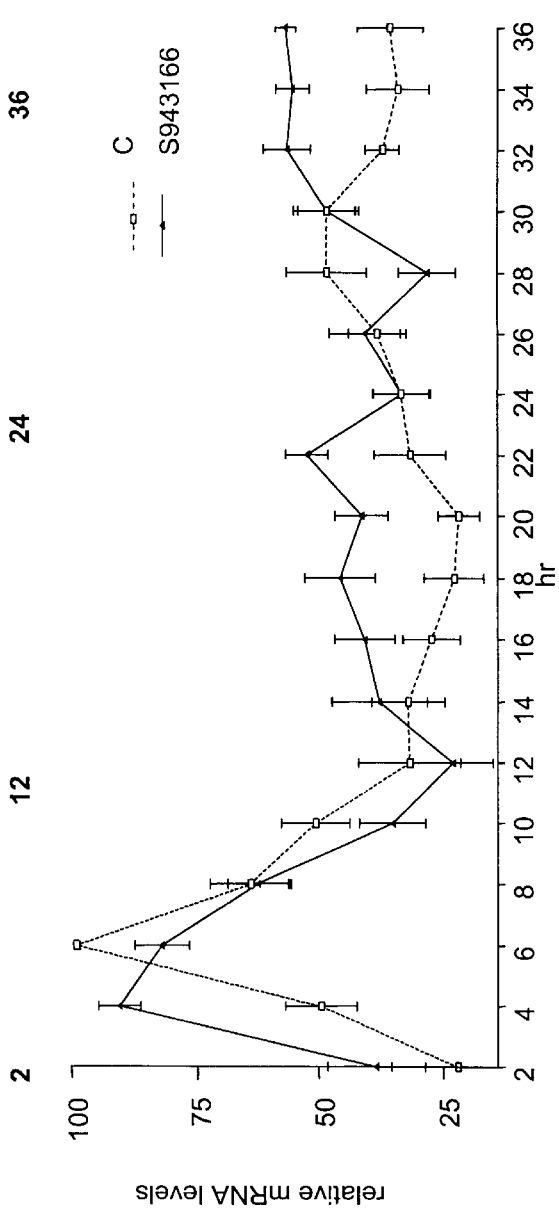

FIG. 11 Human Period mRNA Levels

The top graph provides a pictorial representation of the data presented in the bottom graph. The bottom axis is time in hours; the other axis is the relative real-time mRNA levels of hPER1 Rat1 fibroblast or Rat SCN cells as determined by RT-PCR. Two test compounds are represented; the test compound represented by boxes is "C" which is added to the cells at 10 uM, the second test compound is represented by triangles is S943166 which is added to the cells at 10 uM. These results show that the the test compound, S943166, alters the circadian rhythm of cells by shifting the mRNA oscillation of hPER1, and shorten the circadian rhythm to about 20 hrs.

DETAILED DESCRIPTION OF THE INVENTION

The present invention is directed to methods to identify test compounds that alter circadian rhythms of mammals, and more specifically, directed to methods to determine the ability of a test compound to alter hCKI δ and/or ε phosphorylation of a human Period protein, preferably human Period 1, human Period 2 and/or human Period 3. In addition, the present invention is directed to a method for determining the ability of a test compound to alter degradation of a phosphorylated human Period protein. The present invention is also directed to a method for determine the ability of a test compound to selectively alter phosphorylation, or alternatively degradation, of one or more human Period proteins relative to its ability to alter phosphorylation, or alternatively degradation, of a different human Period protein.

The present invention relates to a method for determining the ability of a test compound to alter hCK I δ and/or ε phosphorylation of hPER1, hPER2 and/or HPER 3, and methods of identifying compounds that alter degradation of hCKI δ and/or ε phosphorylated hPER1, hPER2 and/or hPER 3 in a cell. The present invention also relates to a method for determining the ability of a test compound to alter the stability of hPER1, hPER2 and/or hPER 3, or and increasing protein degradation of hPER1, hPER2 and/or HPER 3. The present invention provides a method for determining the ability of a test compound to alter circadian rhythm of a mammal.

An aspect of the present invention is to determine the ability of a test compound to alter phosphorylation of hPER1, hPER2 and hPER 3 by hCKI δ and/or ε. Another aspect of this invention is determine the ability of a test compound to inhibit phosphorylation of hPER1, hPER2 and hPER 3 by hCKI δ and/or ε, comprising adding a test compound to a screening system comprising a human Period protein selected from the group consisting of hPER1, hPER2 and hPER 3, and hCKI δ and/or ε under conditions which permit phosphorylation, and determining the level of phosphorylation of the human Period protein. In one preferred embodiment, the screening system comprises a source of phosphate. A preferred source of phosphate is ATP.

The term "amino acid" refers to the meaning including either of optical isomers, i.e., an L-isomer and a D-isomer of naturally-occurring and non-naturally-occurring amino acids. Thus, the term "peptide" refers to the meaning including not only peptides constituted by L-amino acids solely but also peptides comprising D-amino acids partially or totally.

Furthermore, the term "amino acid" includes only twenty naturally-occurring amino acid residues which constitute natural proteins, as well as other alpha-amino acids, beta-, gamma- and delta-amino acids, and non-naturally-occurring amino acids, and the like. Thus, the proteins, human Period and human hCKI δ and/or ε, may be modified with one or more amino acid residues conservative amino acid residues, for example, one having a similar charge, polarity or other property of one of the alpha-amino acid residue which constitute natural proteins, as well as other alpha-amino acids residues, and beta-, gamma- and delta-amino acid residues, non-natural amino acid residues, and the like. Examples of suitable beta-, gamma- and delta-amino acids include beta-alanine, gamma-aminobutyric acid and ornithine. Examples of other amino acid residues other than those constituting natural proteins or the non-natural amino acids include 3,4-dihydroxyphenylalanine, phenylglycine, cyclohexylglycine, 1,2,3,4-tetrahydroisoquinolin-3-carboxylic acid or nipecotinic acid.

The terms "hPER1", "hPER2", "hPER3", "hCKI δ" and "hCKIε" includes full length proteins of human Period 1, human Period 2, human Period 3, human Casein Kinase I δ and human Casein Kinase I ε, respectively, alleles and derivatives of hPER1, hPER2, HPER 3, and hCKI δ and/or ε proteins. Derivatives include alternation from naturally-occurring forms of these proteins by one or more different amino acids, truncated proteins, and fusion proteins of the full length or truncated protein containing either 3' or 5'-'tags', as well as naturally-occurring and non-naturally-occurring mutant sequences provided in the literature cited above and submitted to public databases such as in GeneBank. Derivatives of these proteins include proteins which contain a leader, epitope or other protein sequence, such as a Myc™-tagged, his-tagged, or a Flag™ epitope tag sequence. Human Period 1 sequence is accessible under Gene Bank Accession AB002107, NID g2506044, submitted by H. Tei on Mar. 24, 1997. Human Period 1 sequence was also published in Tei, H., et al., *Nature* 389:512–516 (1997). Human Period 2 sequence is accessible under Gene Bank Accession NM003894, NID g4505710, submitted by T. Nagase et al. Human Period 2 sequence was also published in Nagase, T., et al., *DNA Res.* 4(2):141–150 (1997) and in Shearman, L. P., et al., *Neuron* 19(6): 1261–1269 (1997). Human Period 3 genomic sequence is accessible under Gene Bank Accession Z98884. Human Casein Kinase I δ sequence is accessible under Gene Bank Accession U29171. Human Casein Kinase I delta was also published in Kusda, J., et. al, *Genomics* 32:140–143(1996). Human Casein Kinase I ε sequence is accessible under Gene Bank Accession L37043. Human Casein Kinase I epsilon was also published in Fish, K. J., et al., *J. Biol. Chem.* 270:14875–14883(1995). The c-MYC tagged CKI δ was a gift form Dr. David Virshup.

The term "base sequence" refers to RNA sequences as well as DNA sequences encoding hPER1, hPER2, hPER3, or hCKIε, including derivatives thereof.

The proteins "hCKIδ" and "hCKIε" according to the present invention is a protein, or derivative thereof, having substantially similar phosphorylation activity on a human Per protein as described herein. The proteins hCKI δ and/or ε are proteins having substantially similar activity of naturally-occurring hCKI δ and/or ε, alleles and derivatives thereof. hCKI δ and/or ε includes other mammalian Casein Kinase I proteins which retain its kinase activity with respect to hPER1, hPER2, and/or hPER3, or have been modified in such a manner that its ability to phosphorylate hPER1, hPER2, and/or hPER3 is not essentially altered. Human forms of hCKI δ and/or ε are preferred. However, use of other mammalian forms of hCKI δ and/or ε would be acceptable because, for example, human hCKI δ and rat hCKI δ are 97% homologous, and their sequences in the kinase domain (284 amino acid residues) were completely identical. Modified proteins include a truncated forms of hCKI δ and/or ε, derivatives of hCKI δ and/or ε containing amino acid substitions, deletions, additions and the like, which retain the ability to phosphorylate hPER1, hPER2 and/or hPER3. Derivatives of Casein Kinase I include proteins which contain a leader, epitope or other protein sequence, such as a Myc™-tagged, his-tagged, or a Flag™ epitope tag sequence and have hPER1 phosphorylating activity. Such derivatives faciliate purification or enable attachment to Sepharose beads or permit easy detection.

Derivatives of hPER1, hPER2 and/or hPER3 include proteins which contain a leader, epitope or other protein sequence, such as a Myc™-tagged, his-tagged, or a Flag™ epitope tag sequence, which retain the ability to be phosphorylated by hCKIε. Such derivatives faciliate purification or enable attachment to Sepharose beads or permit easy detection. Preferred human Period proteins comprise proteins with one or more hCKIε consensus phosphorylation sequence 'DXXS', where D is a glutamic acid residue, X is any amino acid residue, and S is a serine residue. Phosphorylation occurs at serines fitting the S-$X_n$-S motif, where n is 1, 2, 3 or 4 and may result in hyperphosphorylation. Phosphorylation preferences for casein kinase I are characterized in Flotow, H. and Roach, P. J., *J. Biol. Chem.* 266(6): 3724–3727(1991). In a preferred embodiment of the invention, the human Period protein is capable of hyperphosphorylation. Phosphorylation sites in hPER1 occur at between amino acids 743 and 889 of hPER1, preferably between amino acids 800 and 820 of hPER1 and most preferably between amino acids 808 and 815 of hPER1, or alternatively for the disruption of the putative CKI interaction domain for human PERI at SEQ ID NO 1: IQELSEQIHRLLLQPVH, at amino acids 486–503, for human PER2 at SEQ ID NO 2: IQELTEQIHRLLLQPVH. amino acids 460–477, and/or for human PER3 at SEQ ID NO 3: ITELQEQIYKLLLQPVH. In one embodiment of the invention, preferred derivatives of hPER1, hPER2 and/or hPER3 comprise a phosphorylation site selected from the group consisting of hPER1 amino acids 743 and 889, or for disruption of the putative CKI interaction domain on hPER1 at amino acids 486–503 (SEQ ID NO 1: IQELSEQIHRLLLQPVH,), for human PER2 at amino acids 460–477 (SEQ ID NO 2: IQELTEQIHRLLLQPVH), and for human PER3 at SEQ ID NO 3: ITELQEQIYKLLLQPVH.

The term "protein having protein kinase activity" refers to a protein which is evaluated by one skilled in the art to have protein kinase activity, e.g., a protein which is capable of phosphorylating one or more human Period protein in a screening system. The screening system may be the same, or substantially similar, conditions as set forth in any one of examples below. However, methods of setting up phosphorylation, degradation, or circadian rhythm assays, are well known in the art and the present invention is not intended to be limited to the specific embodiments provided herein.

Proteins to be used in the present invention may be obtained, for example, from human tissue, recombinantly expressed by standard recombinant techniques, and/or optionally chemically modified. Recombinant expression of the proteins is preferred.

"Derivatives" of proteins includes proteins in which an amino group at an amino terminal (N-terminal) or all or a part of amino groups of side chains of amino acids, and/or a carboxyl group at a carboxyl terminal (C-terminal) or all or a part of carboxyl groups of side chains of amino acids, and/or functional groups other than the amino groups and carboxyl groups of the side chains of the amino acids such as hydrogen, a thiol group or an amido group have been modified by appropriate other substituents. The modification by the appropriate other substituents is carried out in order to, for example, protect functional groups in the protein, improve safety or facilitate assaying, such as addition of fuinctional groups to attach a protein to a Sepharose bead. An example is addition of a Flag™ epitope tag sequence added to the primers at the 5' end or his-tagged.

The derivatives of the proteins include:

(1) proteins in which one or more hydrogen atoms of the amino group at the amino terminal (N-terminal) or a part or all of the amino groups of the side chains of the amino acids are replaced by substituted or unsubstituted alkyl groups (which may be straight chain or branched chain or cyclic chain) such as a methyl group, an ethyl group, a propyl group, an isopropyl group, an isobutyl group, a butyl group, a t-butyl group, a cyclopropyl group, a cyclohexyl group or a benzyl group, substituted or unsubstituted acyl groups such as a formyl group, an acetyl group, a caproyl group, a cyclohexylcarbonyl group, a benzoyl group, a phthaloyl group, a tosyl group, a nicotinoyl group or a piperidincarbonyl group, urethane-type protective groups such as a p-nitrobenzyloxycarbonyl group, a p-methoxybenzyloxycarbonyl group, a p-biphenylisopropyl-oxycarbonyl group or a t-butoxycarbonyl group, or urea-type substituents such as a methylaminocarbonyl group, a phenylcarbonyl group or a cyclohexylaminocarbonyl group;

(2) proteins in which the carboxyl groups at the carboxyl terminal (C-terminal) or a part or all of the side chains of the amino acids are esterified (for example, the hydrogen atom(s) are replaced by methyl, ethyl, isopropyl, cyclohexyl, phenyl, benzyl, t-butyl or 4-picolyl), or amidated (for example, unsubstituted amides or $C_1$–$C_6$ alkylarnide such as an methylamide, an ethylamide or an isopropylamide are formed; or (3) proteins in which a part or all of the functional groups other than the amino groups and the carboxyl groups of the side chains of the amino acids such as hydrogen, a thiol group or an amino group are replaced by the substituents described in (1) or a trityl group.

The term "altering" refers to the ability of a test compound to inhibit or enhance phosphorylation of hPER1, hPER2, and/or hPER3 by hCKI δ and/or ε relative to the phosphorylation in the absence of the test compound. Alternatively, "altering" also refers to the ability of a test compound to inhibit or enhance phosphorylation of hPER1, hPER2, and/or hPER3 by hCKI δ and/or ε relative to the phosphorylation of the different compound, such as a standard. It is preferred that the ability of a compound to inhibit or enhance phosphorylation of hPER1, hPER2, and/or hPER3 is determined with respect to a naturally-occuring form of hCKI δ and/or ε protein.

The term "screening system" refers to a set of conditions suitable to permit phosphorylation of hPER1, hPER2, and/or hPER3 by hCKI δ and/or ε. Generally, a screening system contains a ready source of phosphate. A preferred source of phosphate is a ready source of ATP. The screening system may be cell-based or in vitro. Cell-based screening systems include the use of cells which express any or each of hPER1, hPER2, hPER3 and/or hCKI δ and/or ε. A method for screening may be either a cell or a cell-free system. Suitable cell systems include yeast cells, such as *S. cerevisia*, bacterial cells, such as *E. coli*, insect cells, such as those used in bacculoviral expression systems, nematode cells, mammalian cells such as COS cells, lymphocytes, fibroblasts (3Y1 cells, NIH/3T3 cells, Rat1 cells, Balb/3T3 cells, etc.), human embryonic kidney cells, such as 293T cells, CHO cells, blood cells, tumor cells, smooth muscle cells, cardiac muscle cells, brain cells. Preferred cell systems are suprachiasmatic nuclei cells, nerve cells, myelocytes, gliacytes and astrocytes. In a cell based system, if the cell system does not express the human Period protein and/or hCKIε, then the cell must be transfected or transformed to express one or both human Period protein and/or and hCKIε. Alternatively, a cell-free system may be used. Partially purified, or purified hPER1, hPER2, and/or hPER3, and hCKI δ and/or ε may be obtained from recombinant sources which express hPER1, hPER2, and/or hPER3, respectively, and hCKI δ and/or ε, or whereby the underlying base sequence of the original mRNA encoding the protein is modified.

Recombinant expression of a human Period protein and/or hCKI δ and/or ε in a cell may be the result of transfection with one or more suitable expression vectors containing, for example, a promoter and cDNA encoding hPER1, hPER2, hPER3 and/or hCKI δ and/or ε. Cell-based screening systems also include the use of cells in which the human Period protein and/or hCKI δ and/or ε is transuded or transduced into the cell as a fusion protein with a transduction or transducing sequence such as TAT protein obtained from HIV, Antennepedia transduction fragment, or any other means of introducing exogenous protein into a cell.

Preferred in vitro screening systems include aqueous compositions comprising a ready source of phosphate. Preferred in vitro screening systems comprise ATP.

Examples of methods for determining the level of phosphorylation of a human Period protein includes standard methods of detecting the amount of protein phosphorylation, such as use of radiolabeled phosphorous and autoradiography, or indirectly by comparing the amount of radiolabeled phosphorous added and the resulting amount of unbound phosphorous. Alternatively, colormetric or other detection means may be used to determnine the level of phosphorylation. Another suitable method for determining the level of phosphorylation of a human Period protein includes a cell-free system using glutathione Sepharose beads where either the human Period protein or hCKIε is bound to a solid support such as to Sepharose beads, and either the hCKIε or human Period protein is added. In addition, numerous alternative methods for determining the amount of human Period protein after are available, and include the use of $^{35}$S-labeled human Period protein degradation, colormetric assays, elution of bound human Period protein and the like.

The screening methods disclosed herein are particularly useful in that they can be automated, which allows for high through-put screening of large number of test compounds, either randomly designed test compounds or rationally-designed test compounds, in order to identify those test compounds that effectively modulate or alter the level of phosphorylation and/or degradation of the human Period protein, and hence alter the circadian rhythm of a mammal.

The term "mammal" refers to human, primate, canine, porcine, bovine and other higher organisms. Humans and primates are more preferred mammals. Humans are most preferred.

Test compounds for use in the present invention include any biological or small molecule chemical compounds, such as a simple or complex organic molecules, peptides, analogues of peptides, proteins, oligonucleotides, compounds obtained from microorganism culture, naturally-occurring or synthetic organic compounds, and/or naturally-occurring or synthetic inorganic compounds. The choice of test compound to be screened is well within the skill of the art.

The present invention also provides a method for determining the ability of a test compound to alter phosphorylation of one or more human Period proteins, comprising:

(1) adding a test compound to a screening system comprising hCKI δ and/or ε protein and one or more human Period proteins selected from the group consisting of hPER1, hPER2 and hPER3, and (2) determining the level of phosphorylation of human Period protein.

It is also understood that the present includes a method for determining the ability of a test compound to alter phosphorylation of a human Period protein, comprising:

(1) adding a test compound to a screening system comprising hCKI δ and/or ε protein and two or more different hPER proteins selected from the group consisting of hPER1, hPER2 and hPER3, and (2) determining the level of phosphorylation of human Period protein.

Alternatively, the present invention includes a method for determining the ability of a test compound to selectively alter phosphorylation of a human Period protein, comprising:

(1) adding a test compound to a screening system comprising hCKI δ and/or ε protein and a hPER protein selected from the group consisting of hPER1, hPER2 and hPER3, and (2) adding a test compound to a screening system comprising hCKI δ and/or ε protein and a hPER protein selected from the group consisting of hPER1, hPER2 and hPER3, where the hPER protein selected in (2) is not the hPER protein selected in (1);

(3) determining the level of phosphorylation of human Period protein in (1) and (2); and (4) comparing the results obtained in (3) for each human Period protein to determine if the test compound is selective for altering phosphorylation of hPER1, hPER2, and/or hPER3.

Alternatively, the present invention includes a method for determining the ability of a test compound to alter degradation of a human Period protein, comprising:

(1) adding a test compound to a screening system comprising hCKI δ and/or ε protein and a hPER protein selected from the group consisting of hPER1, hPER2 and hPER3, (2) determining the amount of human Period protein after addition of the test compound, and (3) comparing the amount of human Period protein obtained in step (2) with the amount of human Period protein in the screening system.

Alternatively, the present invention includes a method for determining the ability of a test compound to alter degradation of a human Period protein, comprising:

(1) adding a test compound and hCKI δ and/or ε protein to a screening system comprising a hPER protein selected from the group consisting of hPER1, hpER2 and hPER3, (2) determining the amount of human Period protein after addition of the test compound and hCKI δ and/or ε protein, and (3) comparing the amount of human Period protein obtained in step (2) with the amount of human Period protein in the screening system.

Alternatively, the present invention includes a method for determining the ability of a test compound to alter degradation of a human Period protein, comprising:

(1) adding hCKI δ and/or ε protein to a screening system comprising a test compound and a hPER protein selected from the group consisting of hPER1, hPER2 and hPER3, (2) determining the amount of human Period protein after addition hCKI δ and/or ε protein, and (3) comparing the amount of human Period protein obtained in step (2) with the amount of human Period protein in the screening system.

The present invention includes a method of altering degradation of hpER1 by an compound which alters the ability of hCKI δ and/or ε protein to phosphorylate hPER1 at a site between amino acids 743 and 889 of hPER1, preferably between amino acids 800 and 820 of hPER1 and most preferably between amino acids 808 and 815 of hPER1, or alternatively for disruption of the putative CKI interaction domain of human PER1 at SEQ ID NO 1: IQELSEQIHRLLLQPVH, at amino acids 486–503, for human PER2 at SEQ ID NO 2: IQELTEQIHRLLLQPVH, amino acids 460–471, and/or for human PER3 at SEQ ID NO 3: ITELQEQIYKLLLQPVH.

As described below, phosphorylated hPER1 protein is rapidly degraded, therefore the screening method according to the present invention can be used to identify test compounds that selectively activate or inhibit degradation of hPER1. Since phosphorylated hpER2 and hPER3 protein is rapidly degraded, the present method can be used to identify test compounds that selectively activate or inhibit degradation of hPER2 or hPER3, respectively. The present method also provides for a method of determining compounds that selectively activate or inhibit phosphorylation hPER1, hPER2 and/or hPER3, by determining the effect of that compound on activation or inhibition of phosphorylation any of hPER1, hPER2 and/or hPER3, and comparing the results obtained with the same, or a different, test compound.

Also, as phosphorylated hPER1 protein is rapidly degraded, the present method of the invention can be used to identify test compounds that selectively increase or reduce the level of a human Period protein in a cell relative to the level of the same or a different human Period protein in the absence of the test compound. In one preferred embodiment of the invention, the method is used to identify test compounds that selectively increase or reduce the level of a hPER1 in a cell relative to the level hPER1 in the absence of the test compound. In an alternative preferred embodiment of the invention, the method is used to identify test compounds that selectively increase or reduce the level of a hPER2 in a cell relative to the level hPER2 in the absence of the test compound.

In addition, the present invention includes a method to identify test compounds that selectively inhibit the amount of hPER1 degradation in a cell relative to the amount of hPER2 degradation in the presence of the test compound. In an alternative embodiment of the invention, the method is used to identify test compounds that selectively inhibit the amount of hPER2 degradation in a cell relative to the amount of hPER1 degradation in the presence of the test compound.

Alternatively, the present invention can be used to used to identify test compounds that selectively increase or reduce the level of hPER2 and/or hPER3 in a cell relative to the level of hPER2 and/or hPER3, respectively, in the absence of the test compound, or alternatively, relative to the level of a different human Period protein. The present method can be used to identify compounds that selectively increase or reduce the levels of hPER1, hPER2 and/or hPER3 in cell relative to its native level. Comparison of the results of different test compounds on the level of human Period protein may also be after a biological or chemical treatment, such as addition, inhibition, or alteration of endogenous and/or exogenous stimuli, such as light, growth factors, transcription factors, and the like.

Phosphorylated hPER proteins are known to be closely involved in the regulation of the circadian cycle of mammals. Therefore, the present invention can be used to used to identify test compounds that affect, modulate or otherwise change the physiological response of the circadian cycle of a mammal in the absence of a test compound or stimuli. Modulation of circadian cycle of a mammal includes the prevention of the alteration of the normal circadian cycle of a mammal in response to a stimuli in the absence of the test compound. Thus, the present invention includes methods of identifying test compounds capable of preventing alteration of circadian rhythms of mammals in response to stimuli that normally alter the circadian rhythms of a mammal.

The following Examples which demonstrate the effect of human casein kinase I ε (hCKIε) on phosphorylation of human Period 1 may be modified to substitute human Period 2 and/or human Period 3. Similar results are obtained with human casein kinase I hCKI δ.

Purified recombinant hCKIε, but not a kinase negative mutant of hCKIε (hCKIε-K38R), phosphorylates hPER1 in vitro. When co-transfected with wild-type hCKIε in 293T cells, hPER1 shows a significant increase in phosphorylation as evidenced by a shift in molecular mass. hPER1 protein could also be co-immunoprecipitated with transfected hCKIε as well as endogenous hCKIε, indicating physical association between hPER1 and hCKIε proteins in vivo. Furthermore, phosphorylation of hPER1 by hCKIε causes a decrease in protein stability in hPER1. Unphosphorylated hPER1 remains stable in the cell throughout a 24-hr cycle, whereas phosphorylated hPER1 has a half-life of approximately 12 hr. Using various hPER1 truncation mutants, potential phosphorylation sites in hPER1 are amino acids 743 through 889, which contain a CKI consensus phosphorylation site.

To investigate whether hCKIε, the mammalian homologue of Drosophila DBT could phosphorylated hPER1, recombinant his-tagged wild-type hCKIε is expressed in from *E. coli*, purified and assayed for its ability to phosphorylate a pair of known substrates, casein and GST-IkBα, as well as hPER1. Recombinant hCKIε phosphorylates both casein and IkBα substrates (FIG. 1A, lanes 2 and 3). Purified wild-type hCKIε autophosphorylates. The ability to autophosphorylate indicates hCKIε activity (FIG. 1A, lanes 1 and 2). Phosphorylation is not observed when recombinant hCKIε is absent (FIG. 1A, lanes 7 and 8).

A kinase negative mutant of hCKIε-K38R, in which lysine 38 in the ATP binding domain is mutated to an arginine, is assayed for phosphorylation of both casein and IkBα substrates. hCKIε-K38R does not have autophosphorylating activity and does not phosphorylate either casein or GST-IkBα substrates (FIG. 1A, lanes 4–6). This demonstrates that the previous phosphorylating activity is specific to wild-type hCKIε.

Figure 1B:
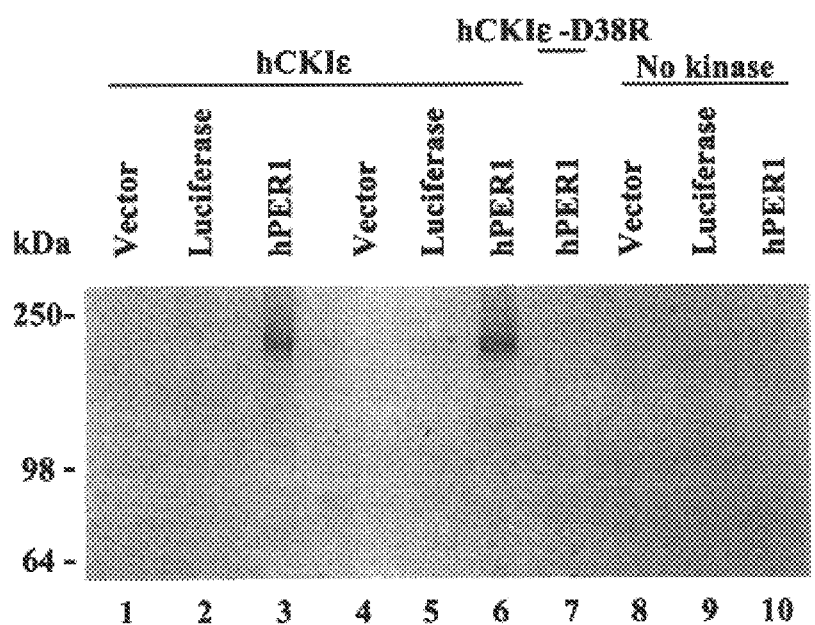
Figure 2A:
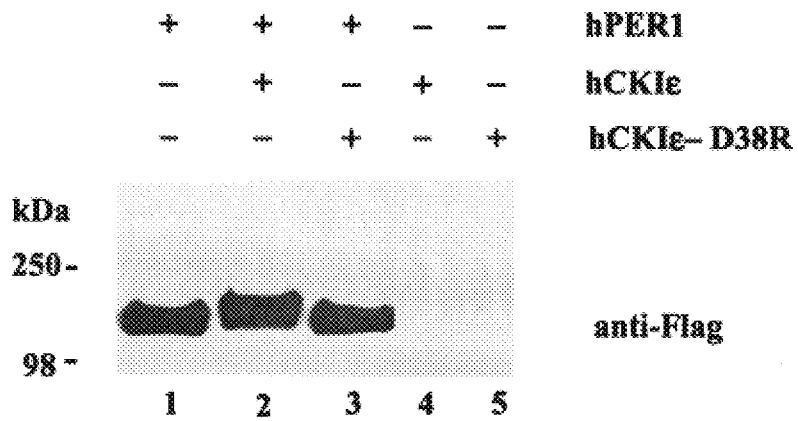
Figure 2B:
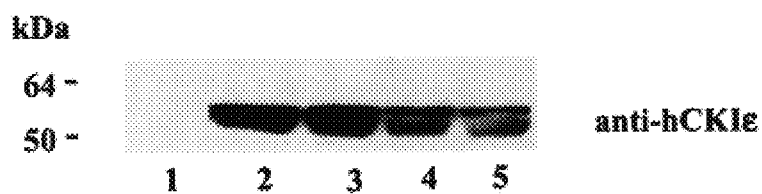

Recombinant hCKIε is also shown to phosphorylate hPER1 in vitro. As shown in FIG. 1B, no phosphorylation is observed in the absence of recombinant hCKIε (lanes 8–10). The presence of hCKIε results in phosphorylation of hPER1, but not Flag-tagged luciferase in vitro (lanes 2 and 3). Phosphorylation of hPER1 is not due to hPER1 associated kinase activity as hCKIε also phosphorylated heat inactivated hPER1 immunoprecipitates (lanes 6). Furthermore, hCKIε-K38R has no kinase activity towards hPER1 (lane 7). Therefore, hCKIε directly phosphorylates hPER1 in vitro.

hCKIε specifically phosphorylates hPER1 in 293T cells co-transfected with flag-tagged hPER1 and either vector control, wild-type hCKIε or hCKIε-K38R. Cells are lysed 24 hr after transfection and the lysates separated on a 3–8% SDS NU-PAGE followed by Western blot analysis. FIG. 2A shows that in cells co-transfected with wild-type hCKIε and hPER1, a significant shift in molecular mass of the hPER1 protein is observed as compared to cells co-transfected with either vector control or hCKIε-K38R (lanes 1–3). Similar shifts in hPER1 molecular mass are always observed in several co-transfection experiments using different percentages of SDS-PAGE. Western blot analysis showed that both wide type hCKIε and hCKIε-K38R proteins are expressed at equivalent levels (FIG. 2B, lanes 2–5).

Figure 2C:
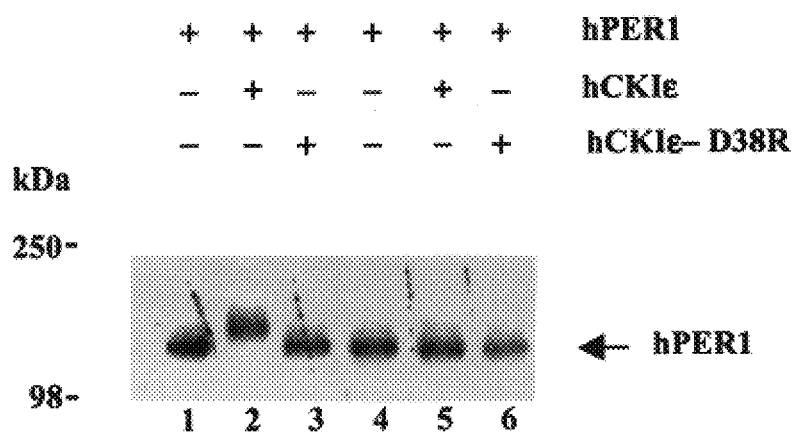

Co-transfected 293T cells with Flag-tagged hPER1 and either vector control, hCKIε or the kinase-negative mutant of hCKIε-K38R and radiolabeled with [$^{35}$S]methionine and cysteine demonstrates the cause for the change in hPER1 molecular mass after phosphorylation. $^{35}$S-labeled hPER1 is immunoprecipitated and either treated or not treated with purified recombinant lambda phosphatase. As shown in FIG. 2C, immunoprecipitated $^{35}$S-radiolabeled hPER1 shows a shift in molecular mass when cells are co-transfected with wild-type hCKIε, but not with vector or kinase-negative hCKIε-K38R controls (lanes 1, 2, and 3). The shift in molecular mass of the protein from co-transfected hPER1 and wild-type hCKIε cells is significantly reduced after 1 hr treatment with lambda phosphatase. This demonstrates that the shift in mobility of hPER1 is due to phosphorylation (FIG. 2C, lanes 2 and 5). After 1 hr treatment with lambda phosphatase, the mobility of all hPER1 from hCKIε co-transfected cells verses vector control and kinase negative co-transfected cells are essentially indistinguishable from each other (FIG. 2C, lanes 4, 5 and 6).

The lambda phosphatase mobility shift is not due to contaminating proteases. Addition of 50 mM sodium fluoride (a phosphatase inhibitor) to the lambda phosphatase reaction blocked the reduction of the mobility shift of hPER1. No other higher molecular mass forms of hPER1 are present in the immunoprecipitates; indicating that the post-translational mobility shift of hPER1 is due to phosphorylation.

Figure 3A:
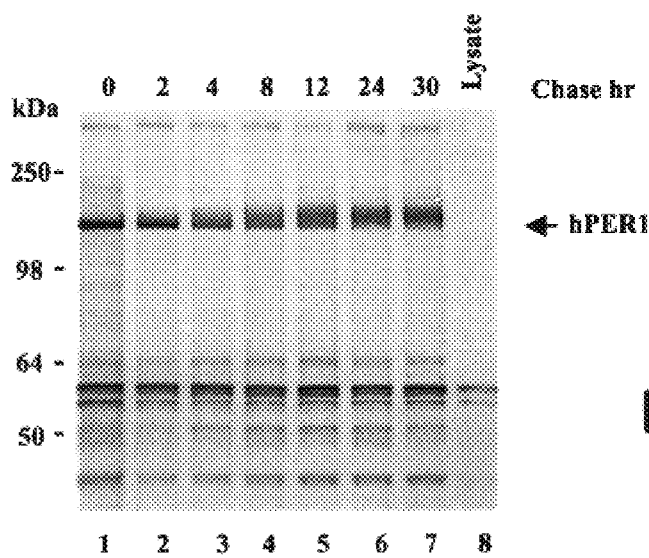
Figure 3B:
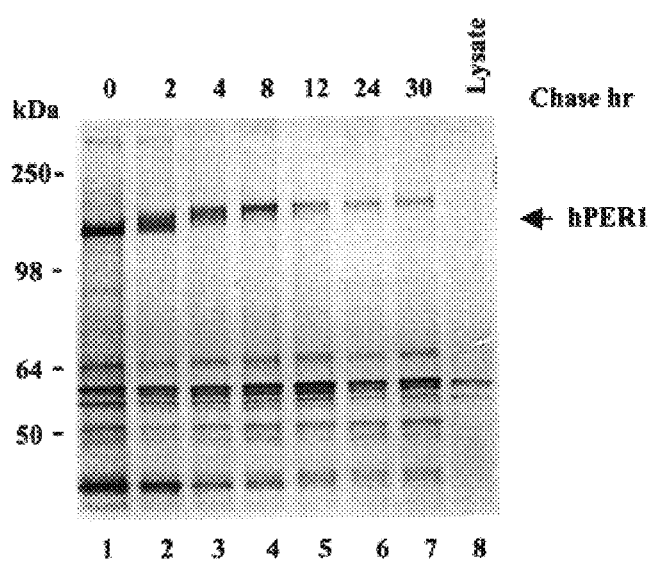
Figure 3C:
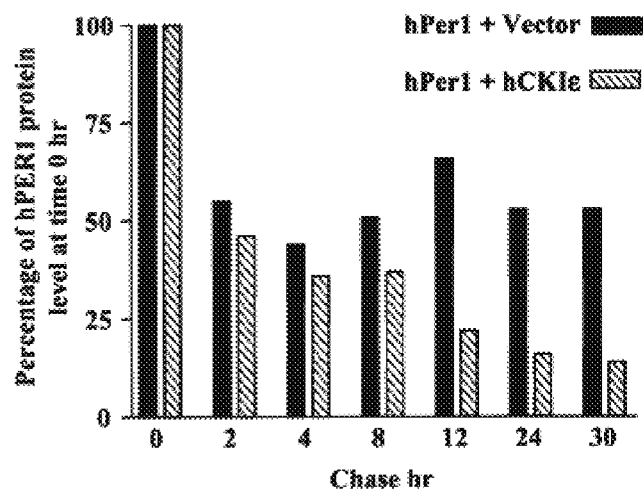

During the circadian cycle, PER protein accumulates and this accumulation leads to its subsequent degradation (Edery, I., et al. (1994) *Proc. Natl. Acad. Sci. USA* 91, 2260–2264, Dembinska, M. E., et al. (1997) *J. Biol. Rhythms* 12, 157–172). During the phase when PER protein accumulates, there is a significant shift in molecular mass that might be due to the phosphorylation of the protein. The mobility shift reaches its maximum just before PER disappears (Edery, I., et al. (1994) supra). Co-transfected 293T cells with expression plasmids encoding both hPER1 and wild-type hCKIε, or vector control are used to demonstrate that phosphorylation of hPER1 results in its instability in cells. Approximately 20 hr post-transfection, the cells are pulse labeled for 30 min with [$^{35}$S]methionine/cysteine and then chased for 0–30 hr. After the appropriate times, hPER1 is harvested, immunoprecipitated and analyzed by SDS-PAGE. As shown in FIG. 3A, cells co-transfected with hPER1 and vector alone showed very little shift in mobility throughout the time course (lanes 1–7). After 12 hr there appeared to be a slight shift in molecular mass as indicated by a smearing of the protein which increased slightly at the 30 hr time point (lanes 1, 5, and 7). The amount of hPER1 present in the control cell remains relatively constant throughout the time courses. At 2 hr post-radiolabeling, approximately 50% hPER1 protein is still present in the cell and this level remains constant throughout the time course (FIG. 3C, solid bars). In contrast to the vector control, cells co-transfected with hPER1 and wt hCKIε showed a shift in mobility as soon as 2 hr post-radiolabeling (FIG. 3B, lanes 1 and 2). This shift in molecular mass continued to become more pronounced throughout the time course with the maximum shift occurring between 24 and 30 hr (FIG. 3B, lanes 2–7). In contrast to the vector control, hPER1 from 293T cells co-transfected with hCKIε showed a decrease in protein stability. Similar to vector control, at the 2-hr time point 50% of total hPER1 from CKIε co-transfected cells is present in the cell. (FIG. 3B, lane 2, and FIG. 3C, crossed-hatched bars). Unlike vector control, only one-half of phosphorylated hPER1 remained in the cell after 12 hr. At 24 hr approximately 14% of phosphorylated hPER1 is present (FIG. 3B, lanes 5 and 6 and FIG. 3C, crossed-hatched bars). This experiment is repeated three times with similar results. Phosphorylation of hPER1 by wild-type hCKIε results in decreased protein stability, and subsequently, in its degradation.

hPER1 and hCKIε physically interact in 293T Cells. 293T cells are co-transfected with Flag-tagged hPER1 and either vector alone or HA-tagged hCKIε. Transfected 293T cells are lysed and hPER1 immunoprecipitated with anti-Flag mAb and then immunoblotted with anti-HA mAb. Alternatively, hCKIε is immunoprecipitated with anti-HA mAb and then immunoblotted with anti-Flag mAb. FIGS.

4A and 4B demonstrate that recombinant hCKIε co-precipitated with hPER1, indicating that hCKIε directly associates with hPER1. 293T cells are transfected with hPER1 only in order to demonstrate that hPER1. Cells are lysed and hPER1 immunoprecipitated with anti-Flag mAb and then immunoblotted with anti-hCKIε mAb. Alternatively, endogenous hCKIε are immunoprecipitated with anti-hCKIε mAb and then immunoblotted with anti-Flag mAb. Endogenous hCKIε co-precipitated with hpER1 indicating a physical association between the two proteins (FIGS. 4C and 4D).

hCKIε phosphorylates hPER1 between amino acids 621 and 889. FIG. 2A shows that the shift in molecular mass of hPER1 is due to phosphorylation by hCKIε. In order to identify the phosphorylation site(s) of hPER1 phosphorylated by hCKIε, truncated versions of hPER1 are prepared as described in FIG. 5A and Materials and Methods, below. These constructs are transfected into 293T cells along with either vector, hCKIε, or hCKIε-K38R, and assayed for a shift in molecular mass. As shown in FIG. 5B, lanes 2, cells co-transfected with both hCKIε and either full length open reading frame hPER1 (ORF), N2, N3 or N4 showed a shift in molecular mass of the protein. Lambda phosphatase treatment of truncated hPER1 protein results in a disappearance of the shift, which is due to phosphorylation by hCKIε hCKIε co-transfected with N1 or C-terminal constructs C1, C2, C5 or C6 did not show a shift in molecular mass of the proteins (FIGS. 5B and 5C, lanes 2). Truncated constructs that showed a shift in molecular mass (ORF, N2, N3, and N4) share a region of homology from amino acids 621 through 889 (see FIG. 5A). Because C1, which contains amino acids 584–743, did not show a shift, hCKIε is phosphorylated hPER1 between amino acids 743 and 889. Several CKI phosphorylation consensus sequences are located throughout hPER1, including one within the region of hPER1 showed above to be phosphorylated by hCKIε, specifically the sequence encompassing amino acids 808–815: DSSSTAPS. All the serines and the threonine could serve as substrate for hCKIε, which might account for the dramatic mobility shift that observed.

MATERIALS AND METHODS

EXAMPLE 1

Plasmid Construction, Expression, and Purification of Proteins

The cDNA encoding wild-type hCKIε is isolated from a human placental cDNA library using previously described methods, Fish, K. J., et al., (1995) *J. Biol. Chem.* 270, 14875–14883. Cloning of hCKIε into bacterial vector (pRST-B-CKIε) and mammalian expression vector (pCEP4-CKIε) is as described previously (Cegielska, A., et al., (1998) *J. Biol. Chem.* 273, 1357–1364, Rivers, A., et al., (1998) *J. Biol. Chem.* 273, 15980–15984). A hemagglutinin (HA) epitope tag (SEQ ID NO 4: YPDYDVPDYA) is added at the 5' end of hCKIε in pCEP4-CKIε. Full-length hPER1 (Tel, H., et al., (1997) *Nature* 389, 512–516) is cut with EcoRI and SalI and ligated into plasmid vector pCMV-Tag™ (Stratagene) to create an in-frame fusion with the Flag tag. Truncated N-terminal mutants (N1, N2, N3, N4, C5) are generated by cutting PER1 with EcoRI/EcoRV, EcoRI/XhoI, EcoRV/XhoI, PvuII/XhoI, or BamHI/SalI, respectively. and ligation into the same vector. To construct mutants C1, C2 and C6, oligonucleotide primers are used in PCR reactions to amplify DNA fragments encoding amino acids 584 to 743, 998 to 1160, or 1161 to 1289, respectively, using hPER1 cDNA as template. The resulting fragments are summarized in Table 1.

TABLE 1

| Full Length and Truncated forms of hPER1 | | |
|---|---|---|
| Designation | First Amino Acid | Last Amino Acid |
| RF | 1 | 1289 |
| N1 | 1 | 485 |
| N2 | 1 | 889 |
| N3 | 486 | 889 |
| N4 | 621 | 889 |
| C1 | 584 | 743 |
| C2 | 998 | 1160 |
| C5 | 1127 | 1289 |
| C6 | 1161 | 1289 |

A Flag™ epitope tag sequence is added to the primers at the 5' end. The PCR products are cloned into the mammalian expression vector pcDNA3 Topo vector™ (Invitrogen). Bacterially expressed histidine-tagged hCKIε and hCKIε-K38R are expressed and purified as described in Cegielska, A., et al., (1998) *J. Biol. Chem.* 273, 1357–1364. The c-MYC tagged CKI δ was provided as a gift from Dr. David Virshup. A protein of greater than 90% homogeneity and with an approximate molecular weight of 54 kDa is purified.

EXAMPLE 2

Transfection and Radiolabeling of 293T Cells

Human embryonic kidney cells 293T are grown in 6 well plate in DMEM supplemented with 10% fetal bovine calf serum (Hyclone). Cells are transfected at a density of approximately 80%, with 2 μg of DNA, using the lipofectAMINE™ reagent (Life Technologies) according to the manufacturers instructions. Transient transfection efficiencies of 293T cells are typically 30–50% as monitored by GFP control plasmid transfection.

293T cells are radiolabeled 16 hr post-transfection with 0.5 μCi/ml [$^{35}$S]methionine/cysteine for 30 min in methionine and cysteine deficient media. Thereafter, cells are ished and cultured in regular DMEM for the time indicated. Cells are lysed using lysis buffer (20 mM tris, 1% Triton X-100™, 0.5% Igepal™, 150 mM NaCl, 20 mM NaF, 0.2 mM Na$_2$VO$_4$, 1 mM EDTA, 1 mM EGTA, Complete protease inhibitor cocktail [Boeringer Mannheim], pH 7.5). Lysates are cleared of cellular debris by centrifugation at 12,000 rpm. Supernatants are collected and stored at −70° C. until use.

EXAMPLE 3

Immunoprecipitations and Western Blot Analysis

Lysates containing equal amounts of protein (100 μg total) are mixed with 5 μl of a 1:500 dilution either of anti-Flag, anti-HA, or anti-hCKIε mAb and incubated overnight at 4° C. After incubation with the antibody, 30 μl of a 1:1 slurry of G-protein sepharose beads is added and incubated for an additional 2–4 hr. The beads are washed five times in lysis buffer and subsequently resuspended in 30 μl of SDS sample buffer with 5 mM DTT, boiled, and analyzed by SDS-PAGE. Western blotting of proteins is performed on either supernatants or immunoprecipitated proteins from transfected 293T cells using either anti-Flag™ (Sigma) at a 1:1000 dilution, anti-HA (Invitrogen) at 1:1000 dilution, or anti-hCKIε (Transduction Laboratories) at a 1:750 dilution as described previously (Yao, Z., et al., (1997) *J. Biol. Chem.* 272, 32378–32383).

EXAMPLE 4

Kinase and Phosphatase Assays hCKIε is assayed for activity using either casein or GST-IkBα as substrate. Casein or ST-IkBα (0.5 µg) is combined with hCKIε (0.1 µg) and 5 µCi [γ-$^{32}$P]ATP (Amersham) in PBS containing 200 nM ATP, 10 mM MgCl$_2$, 0.6 mM EGTA, and 0.25 mM DTT. Reactions are incubated for 30 minutes at room temperature, stopped by the addition of SDS sample buffer, and then analyzed by SDS-PAGE. Because GST-IkBα migrated at a similar position in SDS-PAGE as hCKIε, a slight modification of the protocol was performed. After the 30 min incubation, GST-IkBα is removed from the kinase reaction by the addition of Glutathione-sepharose beads. The beads are washed five times in lysis buffer to remove any contaminating hCKIε before the addition of SDS sample buffer. Gels are stained with Coomassie blue R-250, dried, and autoradiographed.

Immunoprecipitation of $^{35}$S-labeled hPER1 is as described above. Beads containing hPER1 are washed three additional times in phosphatase buffer (100 mM MES, 0.5 mM dithiothreitol DTT, 0.2 mM phenylmethylsulfonyl fluoride, 20 µg/ml aprotinin, 10 µg/ml leupeptin, 10 µg/ml pepstatin A, pH 6.0) and resuspended in 20 µl of phosphatase buffer. The phosphatase treatment is initiated by the addition of a 10× solution of reaction (50 mM Tris-HCL, 0.1 mM EDTA, 5 mM DTT 0.01% Brij 35, 2 mM MnCl$_2$ pH 7.0), and 40 units of purified lambda phosphatase. The reaction is allowed to proceed for 1 hr at 37° C. Inhibition of phosphatase activity is achieved by the addition of 50 mM sodium fluoride. After the appropriate incubations, the reaction is stopped by the addition of SDS sample buffer. The proteins are separated using SDS-PAGE; the gel is dried and autoradiographed. The image is visualized using a Molecular Dynamics PhosphoImager™.

EXAMPLE 5 hCKIε interaction with and phosphorylation of human PER1

The following Examples demonstrate the Materials and Methods used to demonstrate that hCKIε interacts with and phosphorylates human PER2. To summarize these result, when co-transfected with hCKIε in 293T cells, hPER2 shows a significant increase in phosphorylation state as evidenced by $^{32}$P incorporation, as well as a shift in molecular mass. Furthermore, like hCKIε and hPER1, HCKIε co-immunoprecipitates with transfected hPER2. Treatment of transfected cells with the hCKIε inhibitor, CKI-7, results in a decrease of hPER1 and hPER2 phosphorylation. Pulse/chase studies reveal that increased phosphorylation of hPER2 by transfected hCKIε caused hPER2 to be degraded. These data indicate a physical association between hCKIε and the human period proteins in vivo between CKI and human PER1 at SEQ ID NO 1: IQELSEQIHRLLLQPVH, at amino acids 486–503, for human PER2 at SEQ ID NO 2: IQELTEQIHRLLLQPVH, amino acids 460–477, and/or presumably for human PER3 at SEQ ID NO 3: ITELQEQIYKLLLQPVH, and a regulation of period stability through hPER1 and hPER2 phosphorylation.

Materials and Methods for hPer2

EXAMPLE 6

Plasmid Construction, Expression, and Purification of Proteins

Full length open reading frame (ORF) human period 2 is cloned by PCR from a human brain cDNA library from Clonetech using forward primer SEQ ID NO 5: ATCTAGATCTAGAATGAATGGATACGCG-GAATCCG and reverse primer SEQ ID NO 6: TCTGCTC-GAGTCAAGGGGGATCCATTTTCGTCTT. The ORF encodes a 1246 amino acid protein. The DNA is subcloned into the pYGFP living color vector (Clonetech) creating a hPER2-C-terminal YGFP protein. Bacterially expressed histidine-tagged hCKIε are expressed and purified as described above. A protein of greater than 90% homogeneity and with an approximate molecular weight of 54 kDa was purified.

EXAMPLE 7

Transfection of 293T Cells

Transfections of human embryonic kidney cells 293T is done using the methods and materials described above, with the substitution of human Period 2 DNA for that of human Period 1 DNA. Lysates and supernatants are collected and stored as described above.

EXAMPLE 8

Immunoprecipitations and Western Blot Analysis

Lysates are used for immunoprecipitation and Western Blot analysis using the methods and materials described above, with the substitution of hPER2 lysate for that of hPER1 lysate. The results are shown below in Table 2. After co-transfection of hPER2 and hCKIε in 293T cells, cells are lysed 24 h after transfection, immunoprecipitated, and lysates separated on 8% SDS-PAGE followed by Western blot analysis. As shown in Table 2, immunoprecipitation of HA-hCKIε followed by Western blot analysis shows that hCKIε interacts with hPER2 as well as hPER1. Positive denotes interaction, a negative denotes no interaction.

EXAMPLE 9 hCKIε associates with and phosphorylates hPER2

The consequence of PERI phosphorylation is instability and degradation of the protein. Therefore, in order to determine if hCKIε phosphorylates PER2, 293 cells were co-transfected with CKIe and hPER2 or hPER1 as control and proteins were visualized by Western blot analysis. As shown in Table 2 in cells co-transfected with hCKIε and hPER2, a shift in molecular mass of the protein is observed, which is similar to the results seen with hCKIε and hPER1.

TABLE 2

|  | hCKIε alone | hPER2 alone | hCKIε and hPER2 | hCKIε (K38A) and hPER2 |
| --- | --- | --- | --- | --- |
| Interaction with CKIε | – | – | + | + |
| Shift in hPER2 migration | not determined | – | + | – |

To determine if the shift in mobility was due to phosphorylation of hPER2, we performed p32 labeling experiments and assayed for incorporation of p32 label into hPER2. As shown in Table 3, co-transfection of hPER2 or hPER1 with CKIe resulted in the incorporation of p32 into both PER proteins. The amount of p32 incorporation appeared to be greater in hPER1 than hPER2. This difference in hPER1 phosphorylation verses hPER2 could be due to an enhanced kinetic rate of phosphorylation of hPER1 by CKI verses hPER2. Another explanation is that hPER1 has a greater number of CKI consensus phosphorylation sites than hPER2, (9 on hPER1 verses 7 on hPER2).

TABLE 3

|  | hCKIε alone | hPER2 alone | hCKIε and hPER2 | hCKIε (K38A and hPER2 |
| --- | --- | --- | --- | --- |
| P32 incorporation into hPER2 in cpm | 1000 | 750 | 5000 | 3000 |

Phosphorylation of hPER2 leads to protein instability: Phosphorylation of hPER1 results in protein instability and degradation. Since hPER2 is similarly phosphorylated by hCKIε, in order to determine the effect of phosphorylation on hPER2 protein stability, HEK 293 cells are transfected with cDNA encoding either PER2 alone or PER1 alone, or co-transfected with cDNAs encoding both hCKIε and PER2, or hCKIε and PER1. Cells are pulsed with 35-S Methionine and immunoprecipitated at the times summarized in Table 4, for 32 hours. As shown in Table 4, single transfection of either hPER2 and hPER1 results in either hPER1 or hPER2 being phosphorylated by endogenous kinase and degraded. The half-lives of each protein is approximately 14 hours for hPER1 and 4 hours for hPER2. However, co-transfection of either hPER1 or hPER2 with hCKIε results in a hyperphosphorylation of both proteins. Furthermore, this hyperphosphorylation results in a slight shift and shortening of the protein half-lives of approximately 2–4 hours. hPER2 appears not to be any more stable than hPER1 after phosphorylation with hCKIε even though it appears to be phosphorylated to a lesser degree than hPER1.

TABLE 4

| Time in hours | hPER1 alone* | hPER2 alone* | hCKIε and hPER1* | hCKIε and hPER2* |
| --- | --- | --- | --- | --- |
| 0 | 100 | 100 | 100 | 100 |
| 4 | 59 | 69 | 33 | 44 |
| 6 | 41 | 37 | 24 | 28 |
| 8 | 48 | 29 | 28 | 26 |
| 14 | 43 | 19 | 22 | 10 |
| 18 | 32 | 11 | 15 | 10 |
| 24 | 16 | 7 | 8 | 6 |
| 32 | 13 | 7 | 2 | 7 |

*S-35 labeled hPER1 or hPER2 in cpm over time to determine the half-life of the protein.

EXAMPLE 10

Assay to for hCKI δ and ε Inhibitors

The following assay is used to test compound for their ability to alter phosphorylation of hPER1, thereby increasing hPER1 levels in co-transfected cells and alter rat PER1 cellular mRNA oscillation. Using a hCKIε-Per1 co-transfection (transient) assay, HEK293T cells are grown in six well plates to about 80% confluence and then co-transfected with hCKIε and Per1 or Per2 using Lipofectamine plus reagent (Gibco BRL). After 16 hours, the transfection medium is removed and the cells are dosed with 1, 10, or 30 uM CKI inhibitory and non-active analogue compounds for 16 hr. After an additional 16 hours, the medium is removed and the cells are washed two times with PBS, lysed, centrifuged and supernatents are run on 8–16% or 8% tris glycine gels. Western blots are performed for Flag-tagged hPER1 or GFP-tagged hPer2. The presence of hCK1ε is detected in each sample by Western blotting with anti-HA antibodies.

As shown in FIG. 9 cells co-transfected with hCK1ε and hPER1 and exposed to an increasing concentrations of a control test compound, for example, one that does not inhibit hCK1ε, no increase in hPER1 levels are observed. However, co-transfected cells treated with hCK1ε inhibitors show a relative increase in hPER1 levels in a dose dependent manner. This increase in hPER1 levels is due to an inhibition of CKI phosphorylation activity and a relative decrease in hPER1 phosphorylation followed by an increase in protein stability. If CKI inhibitors alter PER1 protein stability and half-life, it can be reasoned that increasing the cellular PER1 levels will have some effect on the circadian oscillation or cellular cycle.

To test the effect of CKI inhibitors in altering rat PER1 oscillation by quantitative PCR using TaqMan RT-PCR (Perkin Elmer Biosystems), rat-1 fibriblasts are grown in Dulbecco's modified Eagle medium supplemented with 5% fetal calf serum and a mixture of penicillin-streptomycin-glutatamine. SCN cells are grown in Dulbecco's Minimum Eagle medium supplimented with 10% fetal calf serum penicillin-streptomycin-glutamine and 2% glucose. Approximately $5 \times 10^5$ cells are plated in 10 cm petri dishes 3–5 days prior to the experiment. Once the plates are confluent, which is designated as time=0, the medium is exchanged with serum rich medium, i.e. serum containing 50% horse serum. After 2 hours of the serum shock in 50% horse serum, this medium is replaced with serum-free medium. At indicated times, the dishes are washed with PBS and kept frozen at −80° C. until the extraction of whole cell mRNA. hCK1ε inhibitor or control is added at the time when serum-free medium is added.

Whole cell mRNA is extracted by means of RNeasy Midi kit or Rnleasy 96 kit (Qiagen) and Dnase treated (Ambion DNA-free). Quantitative PCR is performed with real-time Taq-Man technology (PE Biosystems) [C. A. Heid et al., *Genomes Res.* 6. M (1996)] and analysed on an ABI PRISM 7700 (T. Takumi et al., Genes Cells 4, 67: 1999). The primers for rPer1 are as follows: Forward SEQ ID NO 7: 5'-TCTGGTTAAGGCTGCTGACAAG-3'; Reverse, SEQ ID NO 8: 5'-GTGTAGCCCCAACCCTGTGA-3', and the TaqMan, probe SEQ ID NO 9: 5'-TCCAAATCCCAGCTGAGCCCGA-3'. As an internal control for the RNA, expression of rActin is examined under the same conditions. Ratios of rPer1 to rActin were calculated and normalized.

As shown in FIG. 10, cells treated with no compound or a test compound that is an inactive hCK1ε small molecule analog show a normal circadian cycle of approximately 24 hr as indicated by PER1 mRNA oscillation. However, cells treated with a test compound that is a CKI inhibitor show an altered daily oscillatory circadian cycle FIG. 11. PER1 mRNA levels in these cells demonstrate a shorten rhythm of about 18 to 20 hours instead of the normal 24 hour cycle. The shortened cycle is the is due to CKI inhibition of phosphorylation, resulting in lower levels of PER phosphorylation. Less phosphorylated PER leads to increased PER protein stability and increased cellular levels of PER, which alters the circadian rhythm of a mammal.

All references cited above are hereby incorporated by reference into this specification.

The above examples are not intended to be limiting and are merely illustrative of the specific embodiments of the invention.

What is claimed:

1. A method for determining the ability of a test compound to alter phosphorylation of one or more human Period proteins, comprising:
   (1) adding a test compound to a screening system comprising hCKI δ and/or ε protein and one or more human Period proteins selected from the group consisting of hPER1, hPER2 and hPER3, and
   (2) determining the level of phosphorylation of human Period protein.

2. The method according to claim 1, wherein the compound alters phosphorylation of human Period protein by hCKI ε.

3. The method according to claim 1, wherein the compound enhances phosphorylation of the human Period protein by hCKI δ.

4. The method according to claim 1, wherein the screening system is a cell system or a cell-free system.

5. The method according to claim 4, wherein the screening system is a cell-free system.

6. The method according to claim 5, wherein the cell-free system uses partially purified or purified human Period protein, hCKI δ or hCKI ε.

7. The method according to claim 6, wherein the human Period protein and hCKI ε are obtained from recombinant sources.

8. The method according to claim 4, wherein the screening system is a cell-based system.

9. The method according to claim 8, wherein the cell-based system is a prokaryotic cell.

10. The method according to claim 9, wherein the prokaryotic cell is a bacterial cell.

11. The method according to claim 4, wherein the cell-based system is a eukaryotic cell.

12. The method according to claim 11, wherein the eukaryotic cell is a yeast cell.

13. The method according to claim 12, wherein the yeast cell is *S. cerevisia*.

14. The method according to claim 11, wherein the cell-based system is an insect cell.

15. The method according to claim 11, wherein the cell-based system is a mammalian cell.

16. The method according to claim 15, wherein the mammalian cell is a human cell.

17. The method according to claim 15, wherein the mammalian cell is a lymphocyte cell, fibroblast cell, tumor cell, smooth muscle cell, cardiac muscle cell, embryonic kidney cell, brain cell, nerve cell, myclocyte cell, gliacyte cell or astrocyte cell.

18. A method for determining the ability of a test compound to alter phosphorylation of a human Period protein, comprising:
   (1) adding a test compound to a screening system comprising hCKI δ and/or ε protein and two or more different hPER proteins selected from the group consisting of hPER1, hPER2 and hPER3, and
   (2) determining the level of phosphorylation of human Period protein.

19. The method according to claim 18, wherein the compound alters phosphorylation of the human Period protein by hCKIε.

20. The method according to claim 18, wherein the compound alters phosphorylation of human Period protein by hCKIδ.

21. The method according to claim 18, wherein the screening system is a cell-free system.

22. The method according to claim 21, wherein the cell-free system uses partially purified or purified, human Period protein, hCKIδ or hCKIε.

23. The method according to claim 22, wherein the human Period protein, hCKIδ or hCKIε are obtained from recombinant sources.

24. The method according to claim 18, wherein the screening system is a cell-based system.

25. The method according to claim 24, wherein the cell-based system is a prokaryotic cell.

26. The method according to claim 25, wherein the prokaryotic cell is a bacterial cell.

27. The method according to claim 24, wherein the cell-based system is a eukaryotic cell.

28. The method according to claim 27, wherein the eukaryotic cell is a yeast cell.

29. The method according to claim 28, wherein the yeast cell is *S. cerevisia*.

30. The method according to claim 27, wherein the eukaryotic cell is an insect cell.

31. The method according to claim 27, wherein the eukaryotic cell is a mammalian cell.

32. The method according to claim 31, wherein the mammalian cell is a human cell.

33. The method according to claim 32, wherein the mammalian cell is a lymphocyte cell, fibroblast cell, tumor cell, smooth muscle cell, cardiac muscle cell, embryonic kidney cell, brain cell, nerve cell, myelocyte cell, gliacyte cell or astrocyte cell.

34. A method for determining the ability of a test compound to selectively alter phosphorylation of a human Period protein, comprising:
(1) adding a test compound to a screening system comprising hCKI δ and/or ε protein and a hPER protein selected from the group consisting of hPER1, hPER2 and hPER3, and
(2) adding a test compound to a screening system comprising hCKI δ and/or ε protein and a hPER protein selected from the group consisting of hPER1, hPER2 and hPER3, where the hPer protein selected in (2) is not the hPer protein selected in (1);
(3) determining the level of phosphorylation of human Period protein in (1) and (2); and
(4) comparing the results obtained in (3) for each human Period protein to determine if the test compound is selective for altering phosphorylation of hPER1, hPER2, and/or hPER3.

35. The method according to claim 34, wherein the compound alters phosphorylation of human Period protein by hCKI ε.

36. The method according to claim 34, wherein the compound enhances phosphorylation of the human Period protein by hCKI δ.

37. The method according to claim 34, wherein the screening system is a cell-based system or a cell-free system.

38. The method according to claim 37, wherein the screening system is a cell-free system.

39. The method according to claim 38, wherein the cell-free system uses partially purified or purified human Period protein, hCKI δ or hCKI ε.

40. The method according to claim 39, wherein the human Period protein and hCKI ε are obtained from recombinant sources.

41. The method according to claim 37, wherein the screening system is a cell-based system.

42. The method according to claim 41, wherein the cell-based system is a prokaryotic cell.

43. The method according to claim 42, wherein the prokaryotic cell is a bacterial cell.

44. The method according to claim 37, wherein the cell-based system is a eukaryotic cell.

45. The method according to claim 44, wherein the eukaryotic cell is a yeast cell.

46. The method according to claim 45, wherein the yeast cell is *S. cerevisia*.

47. The method according to claim 37, wherein the cell-based system is an insect cell.

48. The method according to claim 37, wherein the cell-based system is a mammalian cell.

49. The method according to claim 48, wherein the mammalian cell is a human cell.

50. The method according to claim 48, wherein the mammalian cell is a lymphocyte cell, fibroblast cell, tumor cell, smooth muscle cell, cardiac muscle cell, embryonic kidney cell, brain cell, nerve cell, myelocyte cell, gliacyte cell or astrocyte cell.

51. A method for determining the ability of a test compound to alter degradation of a human Period protein, comprising:
(1) adding a test compound to a screening system comprising hCKI δ and/or ε protein and a hPER protein selected from the group consisting of hPER1, hPER2 and hPER3,
(2) determining the amount of human Period protein after addition of the test compound, and
(3) comparing the amount of human Period protein obtained in step (2) with the amount of human Period protein in the screening system.

52. A method for determining the ability of a test compound to alter degradation of a human Period protein, comprising:
(1) adding a test compound and hCKI δ and/or ε protein to a screening system comprising a hPER protein selected from the group consisting of hPER1, hPER2 and hPER3,
(2) determining the amount of human Period protein after addition of the test compound and hCKI δ and/or ε protein, and
(3) comparing the amount of human Period protein obtained in step (2) with the amount of human Period protein in the screening system.

53. A method for determining the ability of a test compound to alter degradation of a human Period protein, comprising:
(1) adding hCKI δ and/or ε protein to a screening system comprising a test compound and a hPER protein selected from the group consisting of hPER1, hPER2 and hPER3,
(2) determining the amount of human Period protein after addition hCKI δ and/or ε protein, and
(3) comparing the amount of human Period protein obtained in step (2) with the amount of human Period protein in the screening system.

54. The method according to claim 1, wherein the human Period protein is human Period1.

55. The method according to claim 1, wherein the human Period protein is human Period2.

56. The method according to claim 1, wherein the human Period protein is human Period3.

57. A method for determining the ability of a test compound to alter the circadian rhythm of a mammal, comprising:
(1) adding a test compound to a screening system comprising hCKI δ and/or ε protein and one or more human Period proteins selected from the group consisting of hPER1, hPER2 and hPER3, and
(2) determining the effect on the circadian rhythm of the mammal relative to the circadian rhythm of the mammal in the absence of the test compound.

* * * * *